United States Patent
Jin et al.

(10) Patent No.: US 10,973,246 B2
(45) Date of Patent: Apr. 13, 2021

(54) CHLAMYDOMONAS MUTANTS PRODUCED USING RGEN RNP AND METHOD FOR PREPARING PIGMENT USING THE SAME

(71) Applicant: Industry-University Cooperation Foundation Hanyang University, Seoul (KR)

(72) Inventors: Eon Seon Jin, Seoul (KR); Sang Su Bae, Seoul (KR); Kwang Ryul Baek, Goyang-si (KR); Duk Hyoung Kim, Incheon (KR); Joo Yeon Jeong, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 0 days.

(21) Appl. No.: 16/893,080

(22) Filed: Jun. 4, 2020

(65) Prior Publication Data

US 2020/0315214 A1 Oct. 8, 2020

Related U.S. Application Data

(62) Division of application No. 16/050,012, filed as application No. PCT/KR2017/004268 on Apr. 21, 2017, now Pat. No. 10,709,152.

(30) Foreign Application Priority Data

Apr. 22, 2016 (KR) .................. 10-2016-0049439
Mar. 31, 2017 (KR) .................. 10-2017-0041761
Mar. 31, 2017 (KR) .................. 10-2017-0041762

(51) Int. Cl.
| | | |
|---|---|---|
| A61K 9/00 | (2006.01) | |
| C12P 23/00 | (2006.01) | |
| A23K 20/179 | (2016.01) | |
| A23L 29/00 | (2016.01) | |
| C12R 1/89 | (2006.01) | |
| A23K 10/16 | (2016.01) | |
| C12N 1/12 | (2006.01) | |
| C12N 9/02 | (2006.01) | |
| A61K 9/20 | (2006.01) | |
| A23K 20/174 | (2016.01) | |
| A23L 33/135 | (2016.01) | |

(52) U.S. Cl.
CPC ............ *A23K 20/179* (2016.05); *A23K 10/16* (2016.05); *A23K 20/174* (2016.05); *A23L 29/065* (2016.08); *A23L 33/135* (2016.08); *A61K 9/0053* (2013.01); *A61K 9/2018* (2013.01); *C12N 1/12* (2013.01); *C12N 9/0073* (2013.01); *C12N 9/0077* (2013.01); *C12P 23/00* (2013.01); *C12R 1/89* (2013.01); *C12Y 114/1309* (2013.01); *C12Y 114/15* (2013.01)

(58) Field of Classification Search
None
See application file for complete search history.

(56) References Cited

FOREIGN PATENT DOCUMENTS

| KR | 10-2014-0083998 A | 7/2014 |
|---|---|---|
| KR | 10-1563148 B1 | 10/2015 |
| WO | 2013/032412 A1 | 3/2013 |
| WO | 2015/086795 A1 | 6/2015 |

OTHER PUBLICATIONS

Inmaculada Couso et al., "Efficient Heterologous Transformation of Chlamydomonas reinhardtii npq2 Mutant with the Zeaxanthin Epoxidase Gene Isolated and Characterized from Chlorella zofingiensis", Mar. Drugs, 2012, pp. 1955-1976, vol. 10; doi:10.3390/md10091955.
Kwangryul Baek et al., "DNA-free two-gene knockout in Chlamydomonas reinhardtii via CRISPRCas9 ribonucleoproteins", Scientific Reports, 2017, pp. 1-7, vol. 6, No. 30620, DOI: 10.1038/srep30620.
Wenzhi Jiang et al., "Successful Transient Expression of Cas9 and Single Guide RNA Genes in Chlamydomonas reinhardtii", Eukaryotic Cell, Nov. 2014, pp. 1465-1469, vol. 13, No. 11.
International Search Report of PCT/KR2017/004268 dated Jul. 25, 2017 [PCT/ISA/210].
Notice of Allowance issued in parent U.S. Appl. No. 16/050,012 dated Mar. 10, 2020.
Robert E. Jinkerson et al., "Molecular techniques to interrogate and edit the Chlamydomonas nuclear genome", The Plant Journal, 2015, pp. 393-412, vol. 82, doi: 10.1111/tpj.12801.
Sojung Kim et al., "Highly efficient RNA-guided genome editing in human cells via delivery of purified Cas9 ribonucleoproteins", Genome Research, 2014, pp. 1012-1019, vol. 24, Published by Cold Spring Harbor Laboratory Press; ISSN 1088-9051/14; www.genome.org.

*Primary Examiner* — Padmavathi Baskar
(74) *Attorney, Agent, or Firm* — Sughrue Mion, PLLC

(57) ABSTRACT

A new alga having an improved ability to produce a pigment is disclosed. When the new alga is used, a carotenoid-based pigment, specifically, a xanthophyll can be produced by consuming less energy, so that it is possible to efficiently produce the pigment at the industrial level. The pigment can be applied as a raw material for a food, a health functional food and a medicine, which include the pigment. Since a DNA fragment is not likely to be inserted into a target base sequence or a base sequence other than the target, it is expected that the procedure of constructing the mutant is not regulated as a GMO, so that it is expected that the procedure of constructing the mutant can create a big economic effect in terms of an industry which produces lutein and zeaxanthin by using microalgae.

3 Claims, 14 Drawing Sheets
(5 of 14 Drawing Sheet(s) Filed in Color)
Specification includes a Sequence Listing.

[Figure 1]
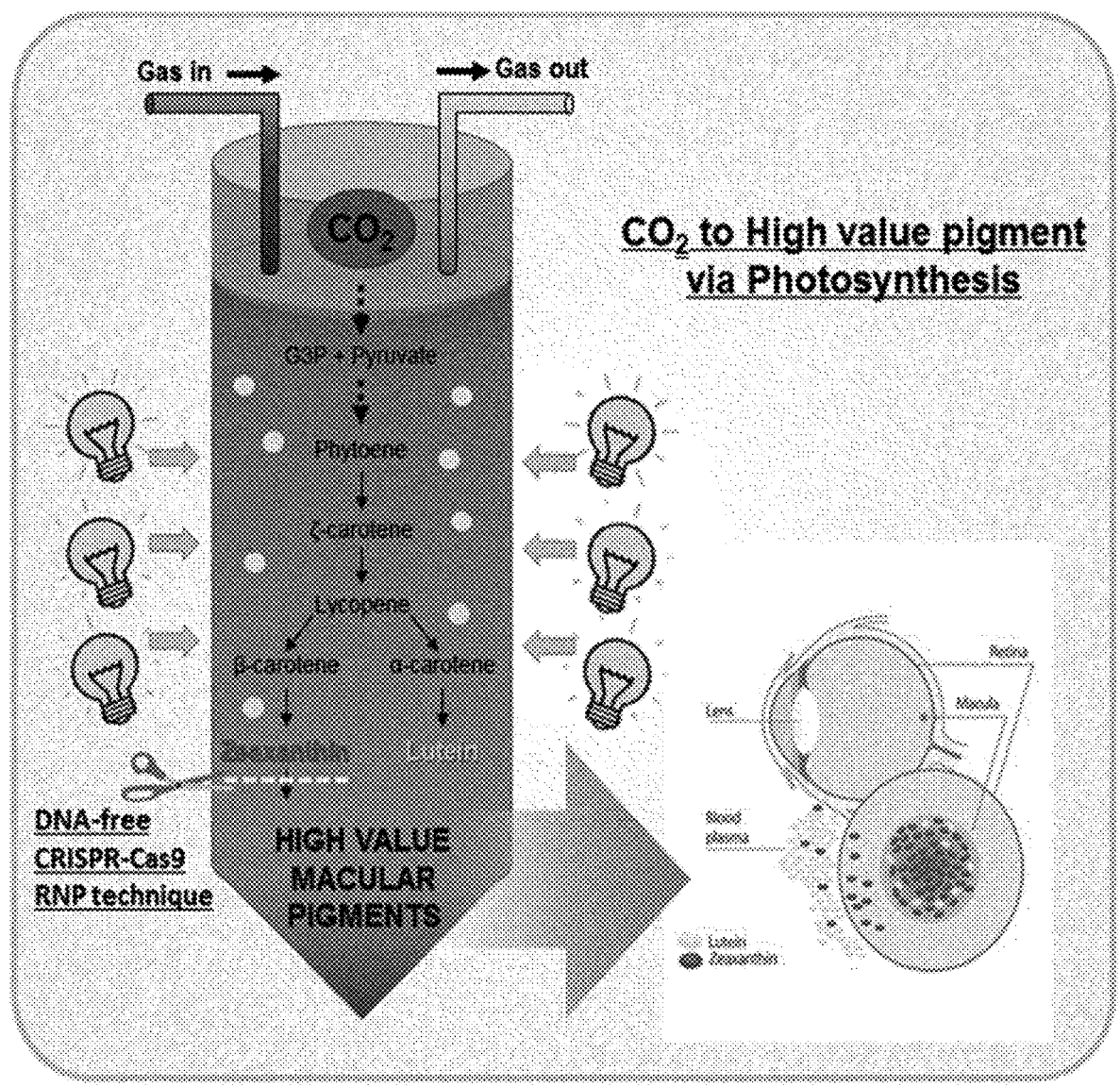

[Figure 2]

Information on zeaxanthin epoxidase (ZEP) gene of Chlamydomonas wild-type and ZEP genes in ZEP mutants 1, 2, and 3

5'UTR / CDS / 3'UTR
Target sequence

>Wild type ZEP gDNA sequence

[sequence illegible]

[Figure 3]

| | sgRNA Target (5' to 3') | Position | Cleavage Position | Direction | GC Contents (w/o PAM) | Out-of-frame Score | Mismatch 0 | Mismatch 1 | Mismatch 2 |
|---|---|---|---|---|---|---|---|---|---|
| RGEN1 | CACCAGCTGCGCGACCGAGCTGG | 638 | 9.732573433 | - | 75 | 84.3 | 1 | 0 | 0 |
| RGEN2 | GCCGTTGCACTTCTGAAGCAGGG | 724 | 13.98509426 | + | 55 | 75.3 | 1 | 0 | 0 |
| RGEN3 | TCCGGCGAACGCACCTGGATGGG | 811 | 17.31698604 | - | 65 | 75.4 | 1 | 0 | 0 |
| RGEN4 | TGGTGGGCGCCGACGGCATCTGG | 2569 | 33.97632617 | + | 75 | 88.2 | 1 | 0 | 0 |
| RGEN5 | CCATGGCTTCGCAGGCATCTCGG | 2868 | 37.26435774 | + | 60 | 71.2 | 1 | 0 | 0 |

| | total | mut | freq(%) | total | mut | freq(%) |
|---|---|---|---|---|---|---|
| RGEN1 | 4276 | 4 | 0.094 | 9541 | 0 | 0 |
| RGEN2 | 16734 | 6 | 0.036 | 19060 | 0 | 0 |
| RGEN3 | 16888 | 77 | 0.456 | 30992 | 0 | 0 |
| RGEN4 | 20274 | 9 | 0.044 | 17138 | 0 | 0 |
| RGEN5 | 15398 | 17 | 0.11 | 7867 | 0 | 0 | b

Control: GCCATCCGCGGCGAGGGCAAGTACCGTGGACCCATC-----CAGGTGCGTTCGCCGGAACACCAACGCGCTTGTTTTTGCTGTGCCGC ZFP-RGEN3:
GCCATCCGCGGCGAGGGCAAGTACCGTGGACCCATCtc---CAGGTGCGTTCGCCGGAACACCAACGCGCTTGTTTTTGCTGTGCCGC  2 ins
GCCATCCGCGGCGAGGGCAAGTACCGTGGACCCAT------CAGGTGCGTTCGCCGGAACACCAACGCGCTTGTTTTTGCTGTGCCGC  1 del
GCCATCCGCGGCGAGGGCAAGTACCGTGGACCCA--------GGTGCGTTCGCCGGAACACCAACGCGCTTGTTTTTGCTGTGCCGC  4 del
GCCATCCGCGGCGAGGGCAAGTACCGTGGACCCATCaacatcCAGGTGCGTTCGCCGGAACACCAACGCGCTTGTTTTTGCTGTGCCGC  6 ins
GCCATCCGCGGCGAGGGCAAGTACCGTGGACCCATCc-----CAGGTGCGTTCGCCGGAACACCAACGCGCTTGTTTTTGCTGTGCCGC  1 ins

[Figure 5]

SpCas9 서열

MGSS██████V█████████AELP██████GIRIPGEKPDKKYSIGLDIGTNSVGWAVITDEYKVPSKK
FKVLGNTDRHSIKKNLIGALLFDSGETAEATRLKRTARRRYTRRKNRICYLQEIFSNEMAKVDDSFFHRL
EESFLVEEDKKHERHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLPGEKKNGLFGNLIA
LSLGLTPNFKSNFDLAEDAKLQLSKDTYDDDLDNLLAQIGDQYADLFLAAKNLSDAILLSDILRVNTEIT
KAPLSASMIKRYDEHHQDLTLLKALVRQQLPEKYKEIFFDQSKNGYAGYIDGGASQEEFYKFIKPILEKM
DGTEELLVKLNREDLLRKQRTFDNGSIPHQIHLGELHAILRRQEDFYPFLKDNREKIEKILTFRIPYYVGPL
ARGNSRFAWMTRKSEETITPWNFEEVVDKGASAQSFIERMTNFDKNLPNEKVLPKHSLLYEYFTVYNE
LTKVKYVTEGMRKPAFLSGEQKKAIVDLLFKTNRKVTVKQLKEDYFKKIECFDSVEISGVEDRFNASLG
TYHDLLKIIKDKDFLDNEENEDILEDIVLTLTLFEDREMIEERLKTYAHLFDDKVMKQLKRRRYTGWGRL
SRKLINGIRDKQSGKTILDFLKSDGFANRNFMQLIHDDSLTFKEDIQKAQVSGQGDSLHEHIANLAGSPAI
KKGILQTVKVVDELVKVMGRHKPENIVIEMARENQTTQKGQKNSRERMKRIEEGIKELGSQILKEHPVE
NTQLQNEKLYLYYLQNGRDMYVDQELDINRLSDYDVDHIVPQSFLKDDSIDNKVLTRSDKNRGKSDNVP
SEEVVKKMKNYWRQLLNAKLITQRKFDNLTKAERGGLSELDKAGFIKRQLVETRQITKHVAQILDSRMN
TKYDENDKLIREVKVITLKSKLVSDFRKDFQFYKVREINNYHHAHDAYLNAVVGTALIKKYPKLESEFVY
GDYKVYDVRKMIAKSEQEIGKATAKYFFYSNIMNFFKTEITLANGEIRKRPLIETNGETGEIVWDKGRDF
ATVRKVLSMPQVNIVKKTEVQTGGFSKESILPKRNSDKLIARKKDWDPKKYGGFDSPTVAYSVLVVAK
VEKGKSKKLKSVKELLGITIMERSSFEKNPIDFLEAKGYKEVKKDLIIKLPKYSLFELENGRKRMLASAGE
LQKGNELALPSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQSITGLYETRI
DLSQLGGD

SpCas9

[Figure 6]
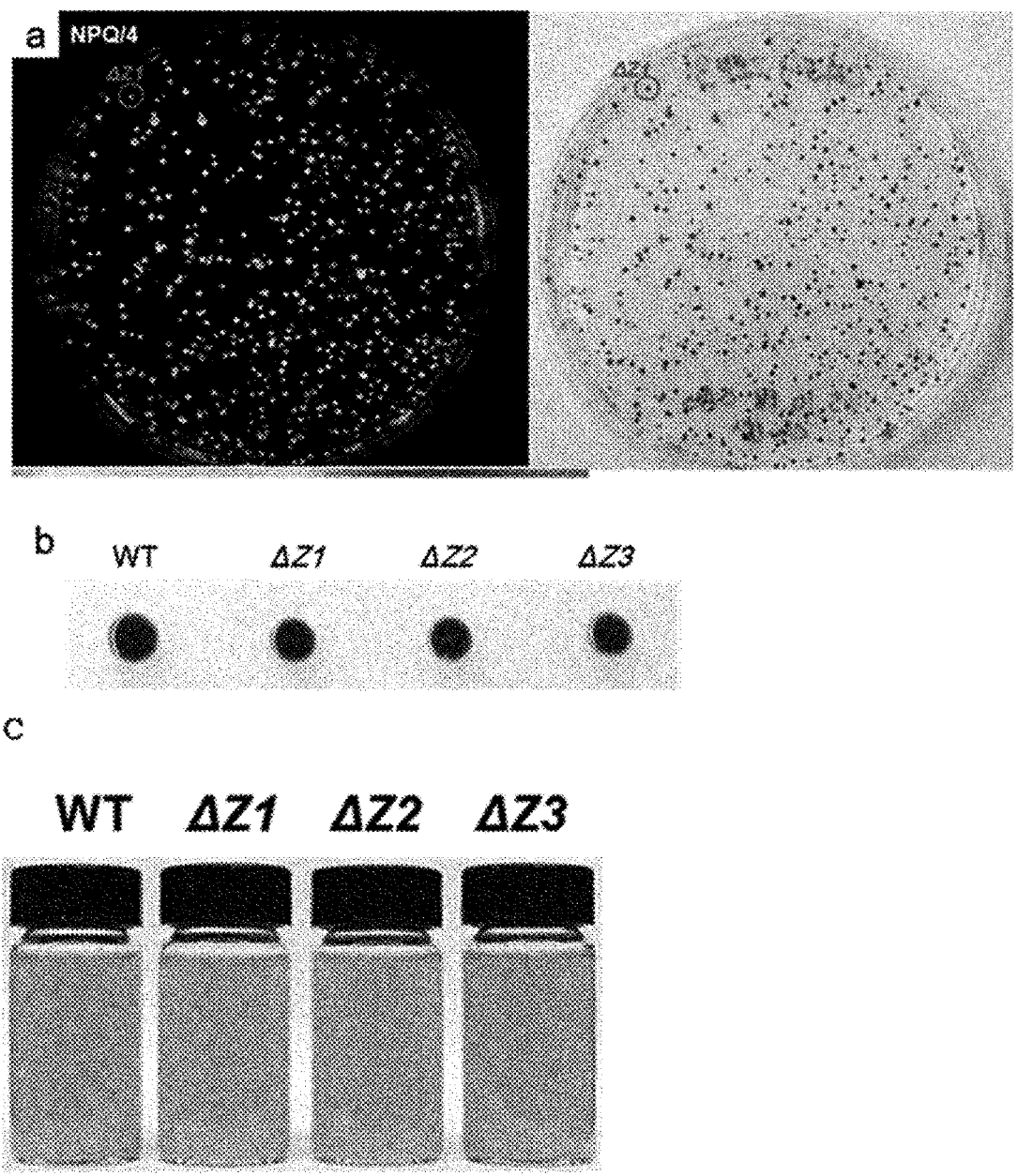

[Figure 7]
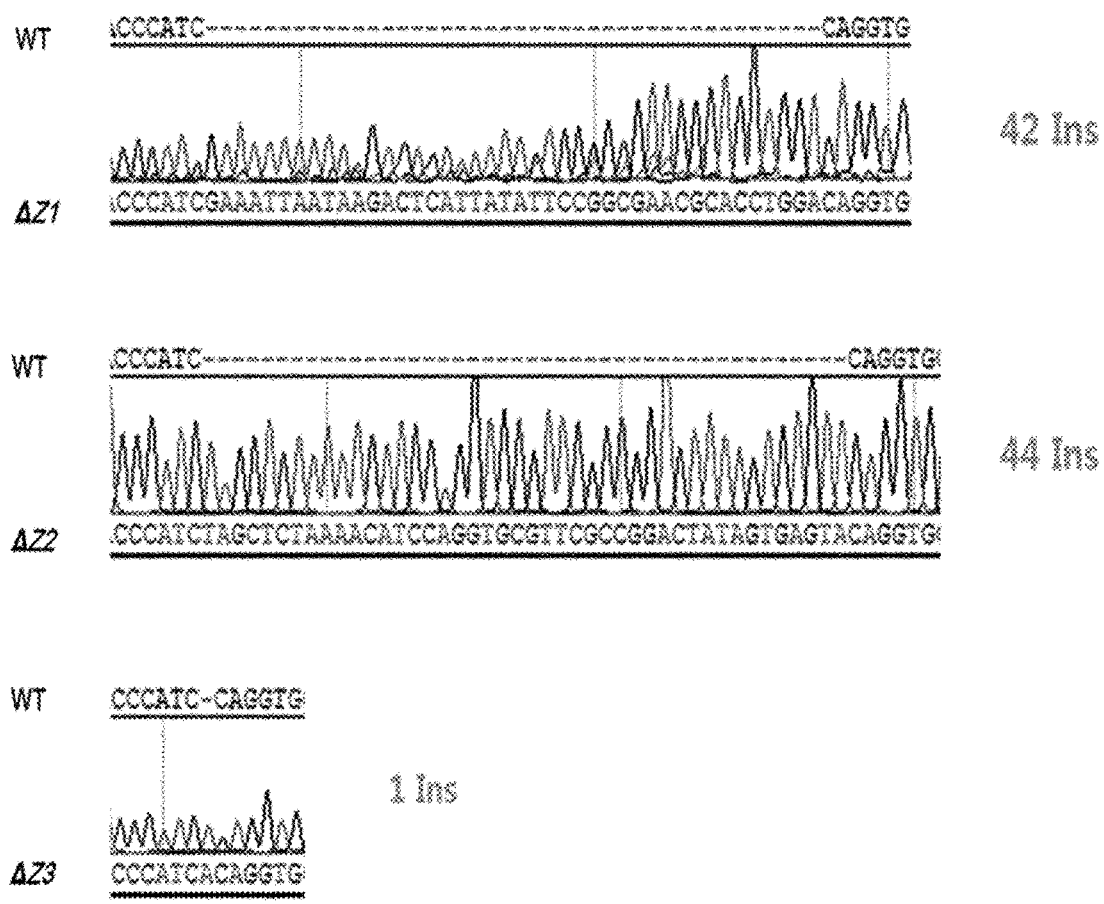

[Figure 8A]

Information on zeaxanthin epoxidase (ZEP) gene of Chlamydomonas wild-type and ZEP genes in ZEP mutants 1, 2, and 3

5'UTR / CDS / 3'UTR
Target sequence
Indel sequence

>ZEP Mutant 1 ZEP gDNA sequence  42bp Insertion

[Figure 8B]

Information on zeaxanthin epoxidase (ZEP) gene of Chlamydomonas wild-type and ZEP genes in ZEP mutants 1, 2, and 3

5' UTR / CDS / 3' UTR
Target sequence
Indel sequence

>ZEP Mutant 2 ZEP gDNA sequence  44bp Insertion

[Figure 8C]

Information on zeaxanthin epoxidase (ZEP) gene of Chlamydomonas wild-type and ZEP mutants 1, 2, and 3

5'UTR / CDS / 3'UTR
Target sequence
Indel sequence

>ZEP Mutant 3 ZEP gDNA sequence    1bp Insertion

【Figure 9】
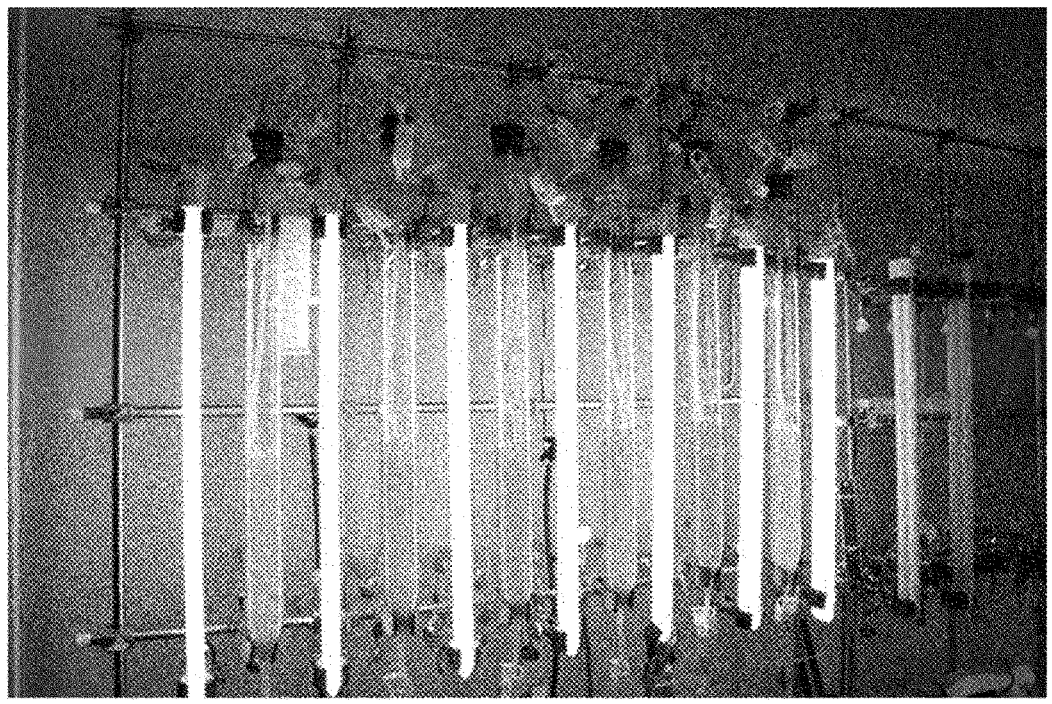
【Figure 10】

[Figure 11]
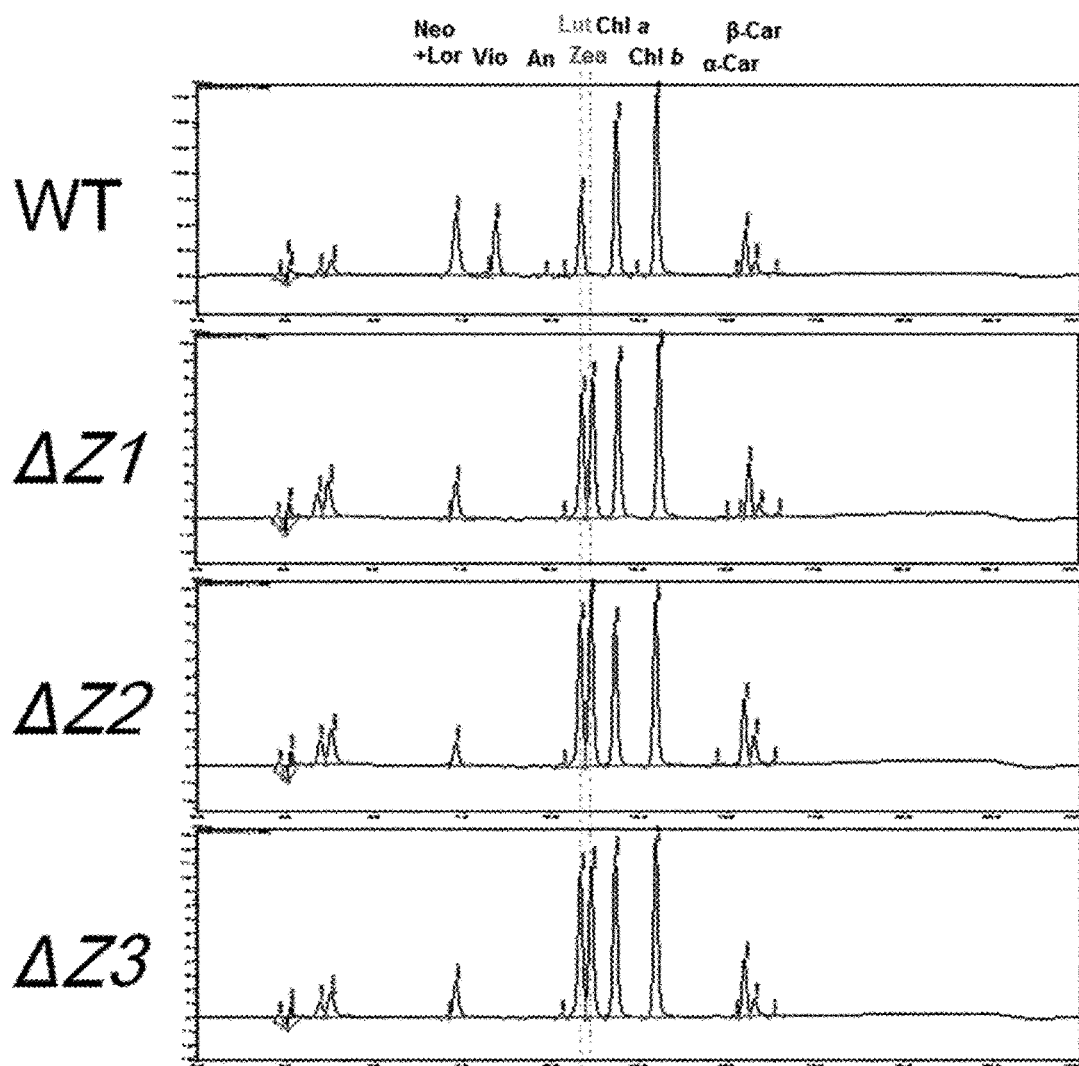

[Figure 12]
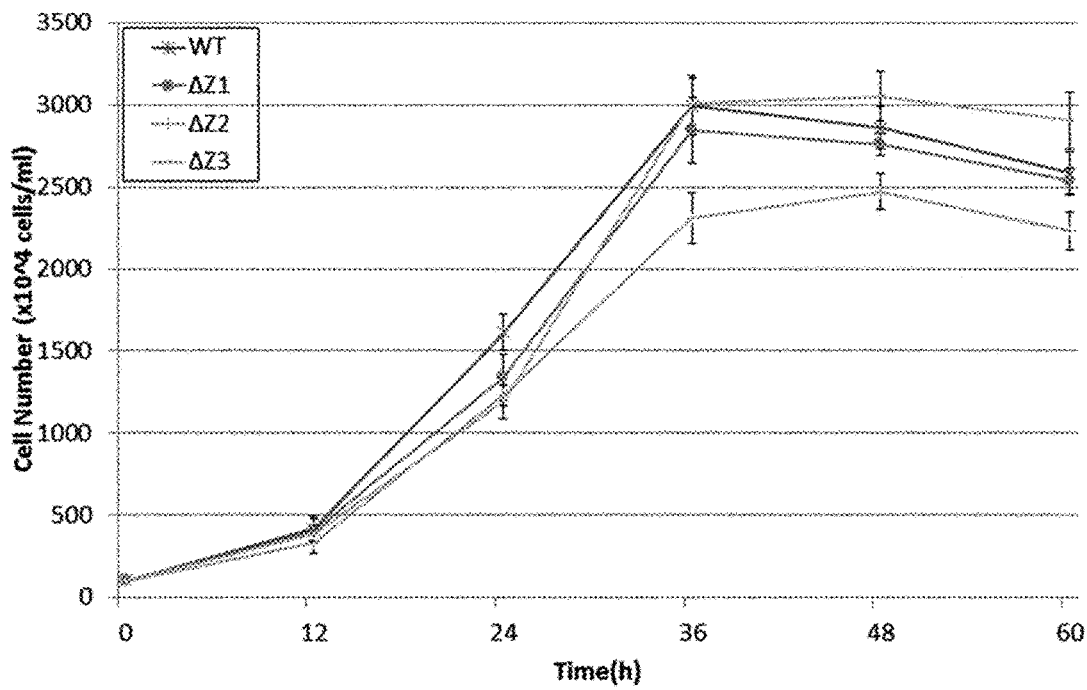
[Figure 13]
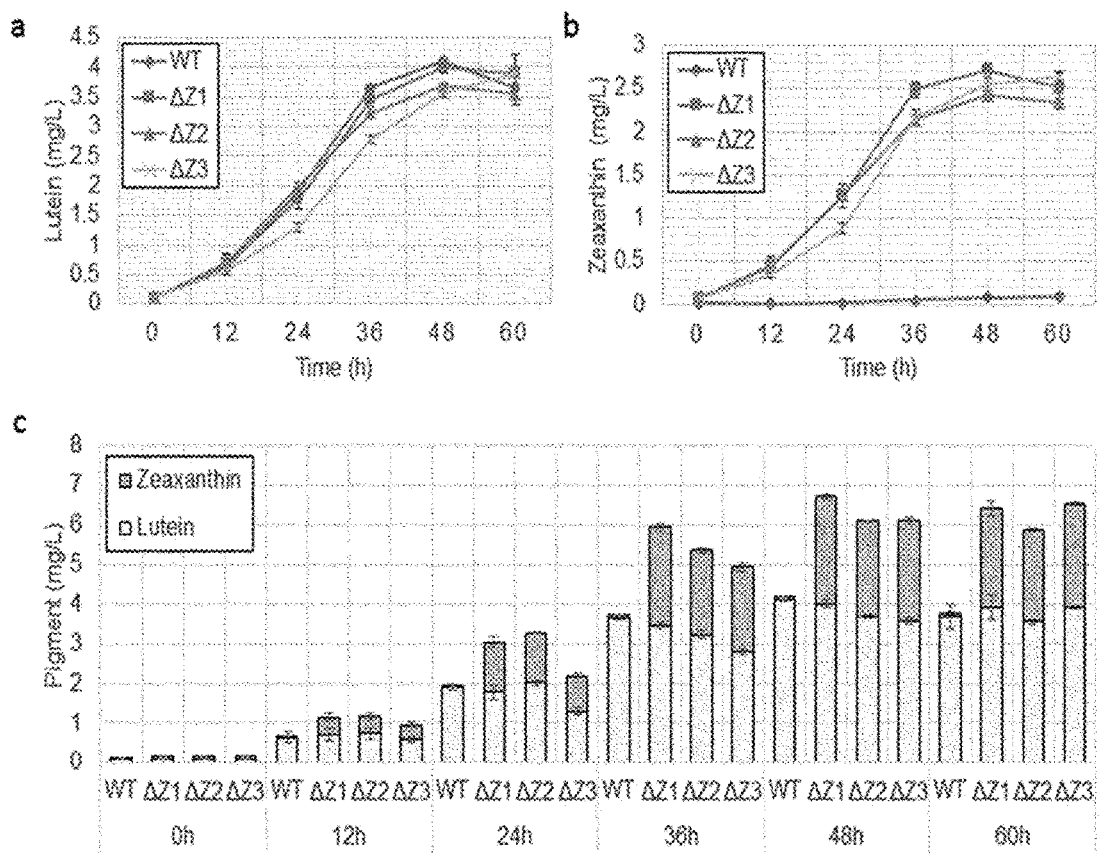

[Figure 14]
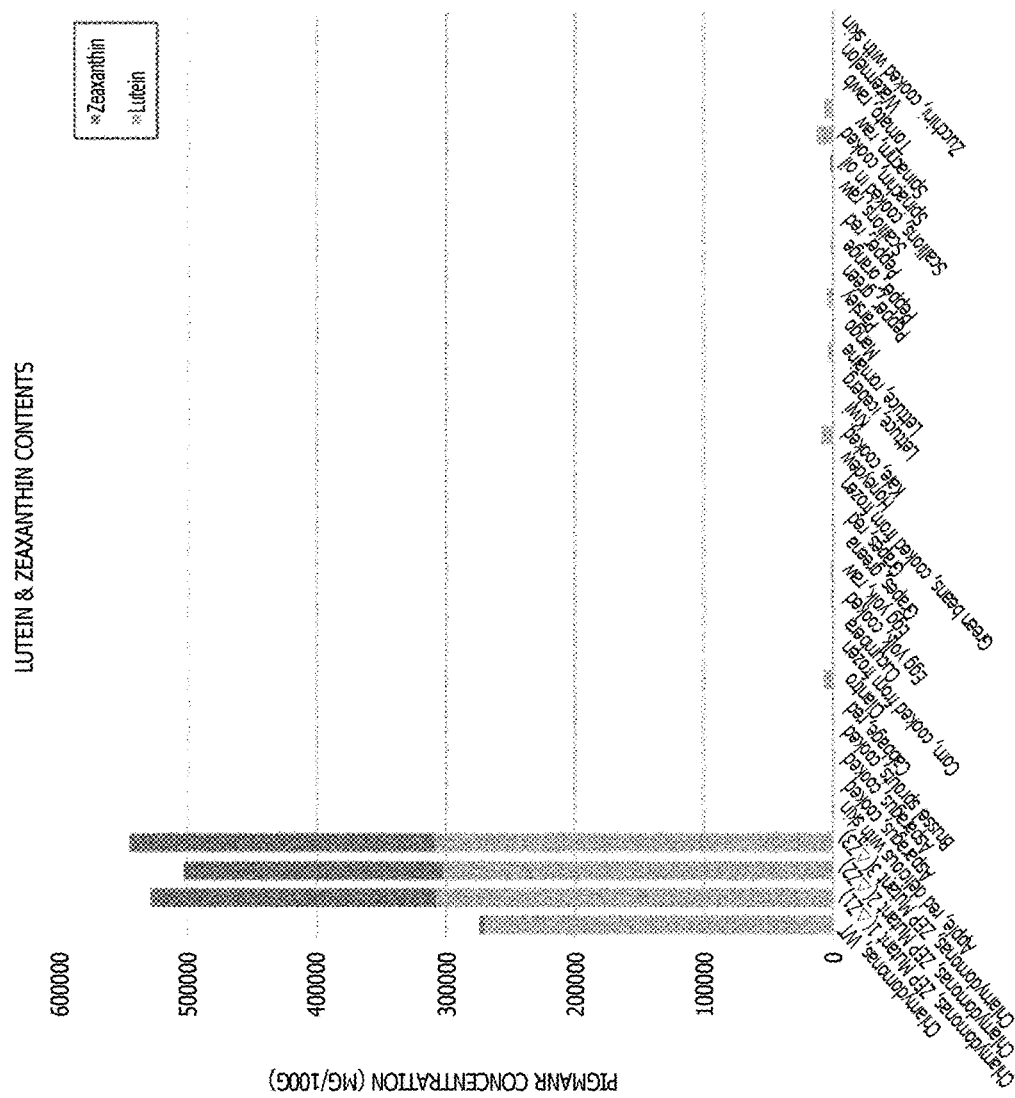

SEQUENCE LISTING

<160> NUMBER OF SEQ ID NOS: 26

<210> SEQ ID NO 1
<211> LENGTH: 6693
<212> TYPE: DNA
<213> ORGANISM: Chlamydomonas reinhardtii

<400> SEQUENCE: 1

```
gcgacgcacg gctgggccaa attcgccaac ggcaggagac caaatcgatc gaggcgatct      60
tgcgaagttc tcggacaaat cgatcgcacc catagtgatt taagcattac atttgcccaa     120
ggcgtgagaa gtgcgaggcc cgaacggcta tgacgccaat gcgcagctta cgacatttaa     180
agcaaattat tcatacatca tacagcacgc ttatgtgaag aaagccagga ttttaggctc     240
tcgccccgat caagacgatc tccccattgc gaagttctcg gtttctttcc ggttcgcctg     300
ctccgtatga tttacctttg cgctacaaca gcgacttaaa cgacctacgt cgccttactg     360
tgtgcgcgta cgtgtttgta gctgtgagat agttttgtcc gcagcgtacc cgcaaataga     420
atgctcgcga gcacttacac gccctgtggc gttcgccagg tggcaggccg cacggttgca     480
gtgcccagca gcttggtcgc gccagtggca gtcgctcggt cgctggggtt ggcgccctac     540
gtccctgtat gtgagccttc tgcggcgctt ccggcctgcc agcagcctag cgggcgtcgt     600
catgttcaga ctgctgccac tctccgtgcc gacaacccca gctcggtcgc gcagctggtg     660
catcagaatg gaaaggggat gaaggttatt atcgccggcg cgggcatcgg cggcctggtg     720
ctagccgttg cacttctgaa gcagggcttc caggttcagg tctttgagcg cgacctgacg     780
gccatccgcg gcgagggcaa gtaccgtgga cccatccagg tgcgttcgcc ggaacaccaa     840
cgcgcttgtt tttgctgtgc cgcgaccatg aactaggcct tatcttgagg tgttagcatg     900
tttagccagc gttggatctg tgtggcgagg ttggggtgag aacccttcct gtgtacctgc     960
tcgggcgtac cttgtgcccc accgctgact ggcttactta atgacaaaac gcaggttcaa    1020
agcaatgcgc tcgctgcgct ggaggctatc gatcccgagg tggccgcgga ggtgctgcgc    1080
gagggctgca tcactggcga ccgtatcaac gggctctgcg acggcctgac tggcgagtgg    1140
tgagtaggca atccagctgt gcatccagtc gcgcggttgc ggaggtcgtc tcgggaaacg    1200
cgacgtggcg tccactcgcc caaggagtgg tctcccgcag cgtggtctcc cgcagctcgg    1260
gtgcaacacc ctgccccctg ccgcgagcgc gctgcgcttc cttatgttgc gcagcggtgt    1320
gagttacaac agcttctgtt gaagagctgt catacgaagc acggcgcgct gtggcgctgc    1380
```

```
agccgtgctg tggaaactcc aacacctcca ccgccagcct gcgcacgcac acgcaataca    1440
ctcgcctcgt gtgcccctc ctcacacaac ggcatgtgac actcagtttt aactcttatt    1500
ttgacagctg agagctacac gcttgggtga atggggaggt ccttgatgtt tcgttgcact    1560
ccgtggctcc ggagtccgtg cggaccgtca cccacaaatg ggagcgcacg gctttcttgt    1620
gctgtctgcc ccgttagcca ctaactgcga atgaccttga cagtttactt tgctattttt    1680
ccttccaggt acgtcaagtt cgacacgttc caccccggcgg tcagcaaggg cctgccggtg   1740
acccgcgtca tcagccgcct cacgctgcag cagatcctgg ccaaagccgt ggagcggtga    1800
gccgtgcgcg cggtgtgatg gctttagcgt cagtgctagc atgggggttg gtgggtggta    1860
atcgcggcgc ccatggccgg gtagcagcgg ccgaaagctg gcgcagagcg cgcgttggac    1920
aagcggtcct gttgccggta tgggcacgag cagggcgctg gtgcgggcaa agggcagagt    1980
ggagttgcag agcagcgctg gcgtcggctg tgcgctctcc aaatggcctc gtggcattct    2040
gacgggacac atcctggaaa atagtagcgc acccaactgc tggtggctcc tcgtacaatc    2100
cccccaattt acaatcgctc gttctggctc gcagctacgg cggccccggc accatccaga    2160
acggctgcaa cgtgaccgag ttcacggagc cgcaacga caccaccggc aacaacgagg      2220
tgagagcgtg ctaagaagag catgcacgtg gagcgtgtaa aattgtgtgg cctgaagcgg    2280
cagtgcctgc ggcatggact aggtggttgc agcatgctgc gcgcgtgggt tgccggtcag    2340
gaaaccgccg gaccgagccg cgcagattca gtcaggagcg gattaggaag tttgaaaaac    2400
agggttcgga gtgtgcaagc gggctcagga gctgtggtgc cttttctacac cggtcgccct    2460 accaggcacc cactgaaact gtaaaaccgt tgctgcgccg gcgatgccct ctacttcact    2520
aggtgactgt gcagctggag gacgggcgca cgtttgcggc cgacgtgctg gtgggcgccg    2580
acggcatctg gtccaagatc cgtaagcagc tcattggcga gaccaaggcc aactacagcg    2640
ggtacacctg ctacaccggt gagattattg accttcaagt tggaaggagg gagcgggggg    2700
agcggaatgg aaggaagcag cgtggacggg gcgcacggag gggaggggac tgcgggtcat    2760
agcgccgcct tgcggggcgt gaggagtgtt gggcggatat tcagttttct ttgcccaaga    2820
tcttcccaca atccgcgtgt gtctgacgcg ggatgtggcc cctgctgcca tggcttcgca    2880
ggcatctcgg actttacgcc ggcggacatt gacattgtgg gctaccgcgt gttcctgggc    2940 aacgccagt actttgtcag cagcgacgtg ggcaacggca agatgcagtg gtgagcggcg    3000
gcgggcgggc gagcgagggc tgcggggtct ggagggtgtg taccgggcgg aagggagggg    3060
aagggagggg aagggaaggc aggatgcagg cgagggcagg atgtgatggt gggaagaggg    3120
cgtggcgagc agcaactgga aaggtggtgg gtaaaaaaat ggtccatgaa tatggctcgg    3180
tacagttcaa agcatggaaa tggaacccgc cgtctgctgc accatgggcg tgagcgggga    3240
gtacgcgact cctggacagc cgtaacaatg cggatggcct caacaagcca ggagcggcac    3300
gaacccagct cacgagcgca cagcgtgcca ggacggcggc cggcaaggat gaaatgtttt    3360
tcctaatata aatgcggact cctgacgcat tatatccatt ttgccactga gccaaagaca    3420
catatataca cgtgcgccgc cgtcctgcgc cacagccgcc tagcgctccg gccgcgcccg    3480
gttccctcgg cgtcatgcgc tggagccccc tcgcaccctg caccgcaaag cccatcaaca    3540
ccacactcgt ccccacaccg cgagtcaccg ccactgcact cgctgtccct caacccgtca    3600
caatctcgcc gacacgcgat aacgaaccca cgcaggtacg gcttccacaa ggagccgtct    3660
ggcggcaccg accccgaggg cagccgcaag gcgcgcctgc tgcagatctt tggccactgg    3720
```

```
aacgacaacg tggtggacct gatcaaggcc acgcccgagg aggacgtgct gcgccgcgac    3780
atctttgaca ggtacggaaa aagggagagc ggggtggctg gagggcggga aagggcgaag    3840
gggcggagaa agaaatgact aggggatggt gttcatttgt gggattgaga ggggtccgcg    3900
gatcccggca gagggcgcca gtggcaaggc gtgggagtcg cggggcggac aatgctgggc    3960
caggggcgcc tagtcacccc gggacactgt ctcagtatgc cgccgtcccg gccgcgccgc    4020
acaggccgcc catcttcacc tggagcaagg gccgcgtggc cctgctgggc gacagcgcgc    4080
acgccatgca gcccaacctg ggccagggcg gctgcatggc cattgaggac gcctacgagc    4140
tggccatcga cctcagccgc gccgtgtccg acaaggccgg aaacgcggcg gcggtggacg    4200
tggagggcgt gctgcgcagc taccaggaca gccgcatttt gcgcgtcagc gccattcacg    4260
gcatggcggg tgagagctgc aaccagcgta gtcgggctgg gctgctgtgg gcagggtcgg    4320
gttgggttgg gcgcacgtgg gcggcgagtg tatgtgcagt gtgacgtgca cactatcata    4380
atactttatg ctcaccgcac cgcgccgcgc cgcaccacgc gccacaggca tggctgcctt    4440 catgccagc acctacaagt gctacctggg cgagggctgg agcaagtggg ttgagggct    4500 gcgcatcccg caccccggcc gcgtggtggg gcggctggtg atgctgctca ccatgcccag    4560
cgtgctggag tgggtgctgg gcggcaacac cgaccacgtg gcgccgcacc gcaccagcta    4620
ctgctcgctg ggcgacaagc ccaaggtgag cggctgccgg gctggggggg ggtggaggga    4680
gaggaggagg attgcgggga acgagggag ggcaaggcag gcgctgcctt cgtggatgca    4740
ccgccccgtc gttagcagga cctcaggaac tcgtccccaa aaccacaaca gaaccccaa    4800 tatcgcctct tccttcactg cttgtcacgc ctggtccgcc gaccgcaggc tttcccgag    4860 agccgcttcc ccgagttcat gaacaacgac gcctccatca tccgctcctc ccacgccgac    4920
tggctgctgg tggcggagcg cgacgccgcc acggccgccg ccgccaacgt gaacgccgcc    4980
accggcagca gcgccgccgc ggccgccgcc gccgacgtga acagcagctg ccagtgcaag    5040
ggcatctaca tggcggactc ggcggccctg gtgggccgct gcggcgccac ctcgcgcccc    5100
gcgctggccg tggacgacgt gcacgtcgcc gagagtcacg cgcaggtctg gcgcggcctc    5160 gccgcctcc cccctcctc gtcgtccgcc tccaccgccg ccgcctctgc gtccgccgcc    5220
tcctctgccg ccagcggcac cgccagcacc ctgggcagct cggagggcta ctggctccgc    5280
gacctgggca gcgccgcgg cacctgggtc aacggcaagc gcctgcccga cggcgccacg    5340
gtgcagctgt ggcccggcga cgcggtggag ttcggccggc accccagcca cgaggtgttc    5400
aaggtgaaga tgcagcacgt gacgctgcgc agcgacgagc tcagcggcca ggcctacacc    5460
acgctcatgg tgggcaagat ccggaacaac gactacgtca tgcccgagtc gcggccggac    5520
ggcggcagcc agcagccggg ccgcctggtg acggcttaag cggcgccgtg cgtaagggcc    5580
ggcttacggg ggcggcagtg tcgctgtgga gggatggtct ggggtgggag gaatgggagg    5640
agagcggcgg gagcccgagg agcggagcgc tggaggcttg cggagcggca gcttgggaag    5700
agctgcggag agaggaagga gcgcagggcg cttggagcac gcgccagatt acgatcacgg    5760
cagcgcgagg cgcgcgtctg acttcgaagt ggtaaggaag atttcatgta tgattgcgtc    5820
gagggacacc gcaagttta cgcgcggcgg agggagcctt gggcatacg acagtacgag    5880 cgggcgttgg tgagaaggtg gtcactccgt atgagaagat ggttactccg taccttcgtg    5940
agaagctgct gcgcacaagt tacgaaccta tctgtgtgga gagcccggta gtatatcagg    6000
ggcgagggtc atgaacgcga gtggcgagtc tgtgagcgcc aatttgttat gcggcataat    6060
ttcgcatcgg ggtattacgt ctacaaaatg ttgagctggc ttagcgcagg aggcaacacc    6120
```

-continued

| | |
|---|---|
| tcaggcagaa tgtacgaatg tgtgcagaag ggcagagtca aggcagaggc ggagaagttg | 6180 |
| tcagggctgt gtgtggtttg gtcagggcgt ggctagatgg atatgagacc cgccgccgtc | 6240 |
| tccagattgt ggcggaggtg gaactctcgg cccccgcgcc agtccccgcg gccagcgcat | 6300 |
| cccgccatgc gggttgttgg ctggtgcatc gcgcggggtg tgctatgagt gtggaaacac | 6360 |
| tatgtcgcgt gtcgtgctga ggtctgttga gaggtttcgt cgtttgtgca tgtcctgtcc | 6420 |
| cggttggagt ttgagcgagg tggttcaaag ttttggatc gcgtgggaga gactgaaacg | 6480 |
| gtttggtgag aatggttgag acagaggttg ggcttggaaa ctggaggaga ggagcagcgt | 6540 |
| aactcgagga cgatgcagta gatgcaccac aacagttgtg gtgggcgcct ggagtaacac | 6600 |
| gcgtgccacc aacacgcaat tacagagatc cgtcatacag gagggatcat atgcgattta | 6660 |
| attttggttt tgcatttgta agacgttttc aca | 6693 |

<210> SEQ ID NO 2
<211> LENGTH: 42
<212> TYPE: DNA
<213> ORGANISM: Artificial Sequence
<220> FEATURE:
<223> OTHER INFORMATION: Chlamydomonas reinhardtii ZEP mutant 1-insert

<400> SEQUENCE: 2

| | |
|---|---|
| gaaattaata agactcatta tattccggcg aacgcacctg ga | 42 |

<210> SEQ ID NO 3
<211> LENGTH: 6735
<212> TYPE: DNA
<213> ORGANISM: Artificial Sequence
<220> FEATURE:
<223> OTHER INFORMATION: Synthetic sequence, ZEP mutant 1

<400> SEQUENCE: 3

| | |
|---|---|
| gcgacgcacg gctgggccaa attcgccaac ggcaggagac caaatcgatc gaggcgatct | 60 |
| tgcgaagttc tcggacaaat cgatcgcacc catagtgatt taagcattac atttgcccaa | 120 |
| ggcgtgagaa gtgcgaggcc cgaacggcta tgacgccaat gcgcagctta cgacatttaa | 180 |
| agcaaattat tcatacatca tacagcacgc ttatgtgaag aaagccagga ttttaggctc | 240 |
| tcgccccgat caagcgatcc tccccattgc gaagttctcg gtttctttcc ggttcgcctg | 300 |
| ctccgtatga tttacctttg cgctacaaca gcgacttaaa cgacctacgt cgccttactg | 360 |
| tgtgcgcgta cgtgtttgta gctgtgagat agttttgtcc gcagcgtacc cgcaaatgaa | 420 |
| atgctcgcga gcacttacac gccctgtggc gttcgccagg tggcaggccg cacgttgca | 480 |
| gtgcccagca gcttggtcgc gccagtggca gtcgctcggt cgctgggtt ggcgccctac | 540 |
| gtccctgtat gtgagccttc tgcggcgctt ccggcctgcc agcagcctag cgggcgtcgt | 600 |
| catgttcaga ctgctgccac tctccgtgcc gacaacccca gctcggtcgc gcagctggtg | 660 |
| catcagaatg gaaaggggat gaaggttatt atcgccggcg cgggcatcgg cggcctggtg | 720 |
| ctagccgttg cacttctgaa gcagggcttc caggttcagg tctttgagcg cgacctgacg | 780 |
| gccatccgcg gcgagggcaa gtaccgtgga cccatcgaaa ttaataagac tcattatatt | 840 |
| ccggcgaacg cacctggaca ggtgcgttcg ccggaacacc aacgcgcttg ttttttgctgt | 900 |
| gccgcgacca tgaactaggc cttatcttga ggtgttagca tgtttagcca gcgttggatc | 960 |
| tgtgtggcga ggttggggtg agaacccttc ctgtgtacct gctcgggcgt accttgtgcc | 1020 |
| ccaccgctga ctggcttact taatgacaaa acgcaggttc aaagcaatgc gctcgctgcg | 1080 |

```
ctggaggcta tcgatcccga ggtggccgcg gaggtgctgc gcgagggctg catcactggc      1140
gaccgtatca acgggctctg cgacggcctg actggcgagt ggtgagtagg caatccagct      1200
gtgcatccag tcgcgcggtt gcggaggtcg tctcgggaaa cgcgacgtgg cgtccactcg      1260
cccaaggagt ggtctcccgc agcgtggtct cccgcagctc gggtgcaaca ccctgccccc      1320
tgccgcgagc gcgctgcgct tgcttatgtt gcgcagcggt gtgagttaca acagcttctg      1380
ttgaagagct gtcatacgaa gcacggcgcg ctgtggcgct gcagccgtgc tgtgaaaact      1440
ccaacacctc caccgccagc ctgcgcacgc acacgcaata cactcgcctc gtgtgccccc      1500
tcctcacaca acggcatgtg acactcagtt ttaactctta ttttgacagc tgagagctac      1560
acgcttgggt gaatggggag gtccttgatg tttcgttgca ctccgtggct ccggagtccg      1620
tgcggaccgt cacccacaaa tgggagcgca cggctttctt gtgctgtctg ccccgttagc      1680
cactaactgc gaatgacctt gacagtttac tttgctattt ttccttccag gtacgtcaag      1740
ttcgacacgt tccacccggc ggtcagcaag ggcctgccgg tgaccgcgt catcagccgc       1800 ctcacgctgc agcagatcct ggccaaagcc gtggagcggt gagccgtgcg cgcggtgtga      1860
tggctttagc gtcagtgcta gcatgggggt tggtgggtgg taatcgcggc gcccatggcc      1920
gggtagcagc ggccgaaagc tggcgcagag cgcgcgttgg acaagcggtc ctgttgccgg      1980
tatgggcacg agcagggcgc tggtgcgggc aaagggcaga gtggagttgc agagcagcgc      2040
tggcgtcggc tgtgcgctct ccaaatggcc tcgtggcatt ctgacgggac acatcctgga      2100
aaatagtagc gcacccaact gctggtggct cctcgtacaa tccccccaat ttacaatcgc      2160
tcgttctggc tcgcagctac ggcggccccg gcaccatcca gaacggctgc aacgtgaccg      2220
agttcacgga gcgccgcaac gacaccaccg gcaacaacga ggtgagagcg tgctaagaag      2280
agcatgcacg tggagcgtgt aaaattgtgt ggcctgaagc ggcagtgcct gcggcatgga      2340
ctaggtggtt gcagcatgct gcgcgcgtgg gttgccggtc aggaaaccgc cggaccgagc      2400
cgcgcagatt cagtcaggag cggattagga agtttgaaaa acagggttcg gagtgtgcaa      2460
gcgggctcag gagctgtggt gcctttctac accggtcgcc ctaccaggca cccactgaaa      2520
ctgtaaaacc gttgctgcgc cggcgatgcc ctctacttca ctaggtgact gtgcagctgg      2580
aggacgggcg cacgtttgcg gccgacgtgc tggtgggcgc cgacggcatc tggtccaaga      2640
tccgtaagca gctcattggc gagaccaagg ccaactacag cgggtacacc tgctacaccg      2700
gtgagattat tgaccttcaa gttggaagga gggagcgggg ggagcggaat ggaaggaagc      2760
agcgtggacg gggcgcacgg aggggagggg actgcgggtc atagcgccgc cttgcggggc      2820
gtgaggagtg ttgggcggat attcagtttt ctttgcccaa gatcttccca caatccgcgt      2880
gtgtctgacg cgggatgtgg cccctgctgc catggcttcg caggcatctc ggactttacg      2940
ccggcggaca ttgacattgt gggctaccgc gtgttcctgg gcaacggcca gtactttgtc      3000
agcagcgacg tgggcaacgg caagatgcag tggtgagcgg cggcgggcgg gcgagcgagg      3060 gctgcgggt ctggagggtg tgtaccgggc ggaagggagg ggaagggagg ggaagggaag       3120
gcaggatgca ggcgagggca ggatgtgatg gtgggaagag ggcgtggcga gcagcaactg      3180
gaaaggtggt gggtaaaaaa atggtccatg aatatggctc ggtacagttc aaagcatgga      3240
aatggaaccc gccgtctgct gcaccatggg cgtgagcggg gagtacgcga ctcctggaca      3300
gccgtaacaa tgcggatggc ctcaacaagc caggagcggc acgaacccag ctcacgagcg      3360
cacagcgtgc caggacggcg gccggcaagg atgaaatgtt tttcctaata taaatgcgga      3420
ctcctgacgc attatatcca ttttgccact gagccaaaga cacatatata cacgtgcgcc      3480
```

```
gccgtcctgc gccacagccg cctagcgctc cggccgcgcc cggttccctc ggcgtcatgc   3540
gctggagccc cctcgcaccc tgcaccgcaa agcccatcaa caccacactc gtccccacac   3600
cgcgagtcac cgccactgca ctcgctgtcc ctcaacccgt cacaatctcg ccgacacgcg   3660
ataacgaacc cacgcaggta cggcttccac aaggagccgt ctggcggcac cgaccccgag   3720
ggcagccgca aggcgcgcct gctgcagatc tttggccact ggaacgacaa cgtggtggac   3780
ctgatcaagg ccacgcccga ggaggacgtg ctgcgccgcg acatctttga caggtacgga   3840
aaaagggaga gcggggtggc tggagggcgg gaaagggcga aggggcggag aaagaaatga   3900
ctaggggatg tgttcattt gtgggattga gaggggtccg cggatcccgg cagagggcgc    3960
cagtggcaag gcgtgggagt cgcggggcgg acaatgctgg gccaggggcg cctagtcacc   4020
ccgggacact gtctcagtat gccgccgtcc cggccgcgcc gcacaggccg cccatcttca   4080
cctggagcaa gggccgcgtg ccctgctgg gcgacagcgc gcacgccatg cagcccaacc    4140
tgggccaggg cggctgcatg gccattgagg acgcctacga gctggccatc gacctcagcc   4200
gcgccgtgtc cgacaaggcc ggaaacgcgg cggcggtgga cgtggagggc gtgctgcgca   4260
gctaccagga cagccgcatt ttgcgcgtca gcgccattca cggcatggcg ggtgagagct   4320
gcaaccagcg tagtcgggct gggctgctgt gggcagggtc gggttgggtt gggcgcacgt   4380
gggcggcgag tgtatgtgca gtgtgacgtg cacactatca taatacttta tgctcaccgc   4440
accgcgccgc gccgcaccac gcgccacagg catggctgcc ttcatggcca gcacctacaa   4500
gtgctacctg ggcgagggct ggagcaagtg ggttgagggg ctgcgcatcc cgcaccccgg   4560
ccgcgtggtg gggcggctgg tgatgctgct caccatgccc agcgtgctgg agtgggtgct   4620
gggcggcaac accgaccacg tggcgccgca ccgcaccagc tactgctcgc tgggcgacaa   4680
gcccaaggtg agcggctgcc gggctggggg ggggtggagg gagaggagga ggattgcggg   4740
gagacgaggg agggcaaggc aggcgctgcc ttcgtggatg caccgccccg tcgttagcag   4800
gacctcagga actcgtcccc aaaaccacaa cagaaccccc aatatcgcct cttccttcac   4860
tgcttgtcac gcctggtccg ccgaccgcag gctttccccg agagccgctt ccccgagttc   4920
atgaacaacg acgcctccat catccgctcc tcccacgccg actggctgct ggtggcggag   4980
cgcgacgccg ccacgccgc cgccgccaac gtgaacgccg ccaccggcag cagcgccgcc    5040
gcggccgccg ccgccgacgt gaacagcagc tgccagtgca agggcatcta catggcggac   5100
tcggcggccc tggtgggccg ctgcggcgcc acctcgcgcc ccgcgctggc cgtggacgac   5160
gtgcacgtcc ccgagagtca cgcgcaggtc tggcgcgggc tcgccggcct cccccctcc    5220
tcgtcgtccg cctccaccgc cgccgcctct gcgtccgccg cctcctctgc cgccagcggc   5280
accgccagca ccctgggcag ctcggagggc tactggctcc gcgacctggg cagcggccgc   5340
ggcacctggg tcaacggcaa gcgcctgccc gacggcgcca cggtgcagct gtggcccggc   5400
gacgcggtgg agttcggccg gcaccccagc cacgaggtgt tcaaggtgaa gatgcagcac   5460
gtgacgctgc gcagcgacga gctcagcggc caggcctaca ccacgctcat ggtgggcaag   5520
atccggaaca cgactacgt catgcccgag tcgcggccgg acggcggcag ccagcagccg   5580
ggccgcctgg tgacggctta agcggcgccg tgcgtaaggg ccggcttacg ggggcggcag   5640
tgtcgctgtg gagggatggt ctggggtggg aggaatggga ggagagcggc gggagcccga   5700
ggagcggagc gctggaggct tgcggagcgg cagcttggga agagctgcgg agagaggaag   5760
gagcgcaggg cgcttggagc acgcgccaga ttacgatcac ggcagcgcga ggcgcgcgtc   5820
```

```
tgacttcgaa gtggtaagga agatttcatg tatgattgcg tcgagggaca ccgcaagttt    5880
tacgcgcggc ggagggagcc ttggggcata caacagtacg agcgggcgtt ggtgagaagg    5940
tggtcactcc gtatgagaag atggttactc cgtaccttcg tgagaagctg ctgcgcacaa    6000
gttacgaacc tatctgtgtg gagagcccgg tagtatatca ggggcgaggg tcatgaacgc    6060
gagtggcgag tctgtgagcg ccaatttgtt atgcggcata atttcgcatc ggggtattac    6120
gtctacaaaa tgttgagctg gcttagcgca ggaggcaaca cctcaggcag aatgtacgaa    6180
tgtgtgcaga agggcagagt caaggcagag gcggagaagt tgtcagggct gtgtgtggtt    6240
tggtcagggc gtggctagat ggatatgaga cccgccgccg tctccagatt gtggcggagg    6300
tggaactctc ggcccccgcg ccagtccccg cggccagcgc atcccgccat gcgggttgtt    6360
ggctggtgca tcgcgcgggg tgtgctatga gtgtggaaac actatgtcgc gtgtcgtgct    6420
gaggtctgtt gagaggtttc gtcgtttgtg catgtcctgt cccggttgga gtttgagcga    6480
ggtggttcaa agttttttgga tcgcgtggga gagactgaaa cggtttggtg agaatggttg    6540
agacagaggt tgggcttgga aactggagga gaggagcagc gtaactcgag gacgatgcag    6600
tagatgcacc acaacagttg tggtgggcgc ctggagtaac acgcgtgcca ccaacacgca    6660
attacagaga tccgtcatac aggagggatc atatgcgatt taattttggt tttgcatttg    6720
taagacgttt tcaca                                                    6735

<210> SEQ ID NO 4
<211> LENGTH: 44
<212> TYPE: DNA
<213> ORGANISM: Artificial Sequence
<220> FEATURE:
<223> OTHER INFORMATION: Chlamydomonas reinhardtii ZEP mutant 2-insert

<400> SEQUENCE: 4
tagctctaaa acatccaggt gcgttcgccg gactatagtg agta                      44

<210> SEQ ID NO 5
<211> LENGTH: 6737
<212> TYPE: DNA
<213> ORGANISM: Artificial Sequence
<220> FEATURE:
<223> OTHER INFORMATION: Synthetic sequence, ZEP mutant 2

<400> SEQUENCE: 5
gcgacgcacg gctgggccaa attcgccaac ggcaggagac caaatcgatc gaggcgatct      60
tgcgaagttc tcggacaaat cgatcgcacc catagtgatt taagcattac atttgcccaa     120
ggcgtgagaa gtgcgaggcc cgaacggcta tgacgccaat gcgcagctta cgacatttaa     180
agcaaattat tcatacatca tacagcacgc ttatgtgaag aaagccagga ttttaggctc     240 tcgcccgat caagacgatc tccccattgc gaagttctcg gtttctttcc ggttcgcctg      300
ctccgtatga tttacctttg cgctacaaca gcgacttaaa cgacctacgt cgccttactg     360
tgtgcgcgta cgtgtttgta gctgtgagat agttttgtcc gcagcgtacc cgcaaataga     420
atgctcgcga gcacttacac gccctgtggc gttcgccagg tggcaggccg cacggttgca     480
gtgcccagca gcttggtcgc gccagtggca gtcgctcggt cgctgggggtt ggcgccctac    540 gtccctgtat gtgagccttc tgcggcgctt ccggcctgcc agcagcctag cgggcgtcgt     600
catgttcaga ctgctgccac tctccgtgcc gacaaccca gctcggtcgc gcagctggtg      660
catcagaatg gaaggggat gaaggttatt atcgccggcg cgggcatcgg cggcctggtg      720
ctagccgttg cacttctgaa gcagggcttc caggttcagg tctttgagcg cgacctgacg     780
```

```
gccatccgcg gcgagggcaa gtaccgtgga cccatctagc tctaaaacat ccaggtgcgt      840
tcgccggact atagtgagta caggtgcgtt cgccggaaca ccaacgcgct tgtttttgct      900
gtgccgcgac catgaactag gccttatctt gaggtgttag catgtttagc cagcgttgga      960
tctgtgtggc gaggttgggg tgagaaccct tcctgtgtac ctgctcgggc gtaccttgtg     1020
ccccaccgct gactggctta cttaatgaca aaacgcaggt tcaaagcaat gcgctcgctg     1080
cgctggaggc tatcgatccc gaggtggccg cggaggtgct gcgcgagggc tgcatcactg     1140
gcgaccgtat caacgggctc tgcgacggcc tgactggcga gtggtgagta ggcaatccag     1200
ctgtgcatcc agtcgcgcgg ttgcggaggt cgtctcggga aacgcgacgt ggcgtccact     1260
cgcccaagga gtggtctccc gcagcgtggt ctcccgcagc tcgggtgcaa caccctgccc     1320
cctgccgcga gcgcgctgcg cttgcttatg ttgcgcagcg gtgtgagtta caacagcttc     1380
tgttgaagag ctgtcatacg aagcacggcg cgctgtggcg ctgcagccgt gctgtggaaa     1440
ctccaacacc tccaccgcca gcctgcgcac gcacacgcaa tacactcgcc tcgtgtgccc     1500
cctcctcaca caacggcatg tgacactcag ttttaactct tattttgaca gctgagagct     1560
acacgcttgg gtgaatgggg aggtccttga tgtttcgttg cactccgtgg ctccggagtc     1620
cgtgcggacc gtcacccaca aatgggagcg cacggctttc ttgtgctgtc tgccccgtta     1680
gccactaact gcgaatgacc ttgacagttt actttgctat ttttccttcc aggtacgtca     1740
agttcgacac gttccacccg gcggtcagca agggcctgcc ggtgacccgc gtcatcagcc     1800
gcctcacgct gcagcagatc ctggccaaag ccgtggagcg gtgagccgtg cgcgcggtgt     1860
gatggcttta gcgtcagtgc tagcatgggg gttggtgggt ggtaatcgcg gcgcccatgg     1920
ccgggtagca gcggccgaaa gctggcgcag agcgcgcgtt ggacaagcgg tcctgttgcc     1980
ggtatgggca cgagcagggc gctggtgcgg gcaaagggca gagtggagtt gcagagcagc     2040
gctggcgtcg gctgtgcgct ctccaaatgg cctcgtggca ttctgacggg acacatcctg     2100
gaaaatagta gcgcacccaa ctgctggtgg ctcctcgtac aatcccccca atttacaatc     2160
gctcgttctg gctcgcagct acggcggccc cggcaccatc cagaacggct gcaacgtgac     2220
cgagttcacg gagcgccgca acgacaccac cggcaacaac gaggtgagag cgtgctaaga     2280
agagcatgca cgtggagcgt gtaaaattgt gtggcctgaa gcggcagtgc ctgcggcatg     2340
gactaggtgg ttgcagcatg ctgcgcgcgt gggttgccgg tcaggaaacc gccggaccga     2400
gccgcgcaga ttcagtcagg agcggattag gaagtttgaa aaacagggtt cggagtgtgc     2460
aagcgggctc aggagctgtg gtgcctttct acaccggtcg ccctaccagg cacccactga     2520
aactgtaaaa ccgttgctgc gccggcgatg ccctctactt cactaggtga ctgtgcagct     2580
ggaggacggg cgcacgtttg cggccgacgt gctggtgggc gccgacggca tctggtccaa     2640
gatccgtaag cagctcattg gcgagaccaa ggccaactac agcgggtaca cctgctacac     2700
cggtgagatt attgaccttc aagttggaag gaggagcgg ggggagcgga atggaaggaa     2760
gcagcgtgga cggggcgcac ggaggggagg ggactgcggg tcatagcgcc gccttgcggg     2820
gcgtgaggag tgttgggcgg atattcagtt ttctttgccc aagatcttcc cacaatccgc     2880
gtgtgtctga cgcgggatgt ggcccctgct gccatggctt cgcaggcatc tcggacttta     2940
cgccggcgga cattgacatt gtgggctacc gcgtgttcct gggcaacggc cagtactttg     3000
tcagcagcga cgtgggcaac ggcaagatgc agtggtgagc ggcggcgggc gggcgagcga     3060
gggctgcggg gtctggaggg tgtgtaccgg gcggaaggga ggggaaggga ggggaaggga     3120
```

```
aggcaggatg caggcgaggg caggatgtga tggtgggaag agggcgtggc gagcagcaac      3180
tggaaaggtg gtgggtaaaa aaatggtcca tgaatatggc tcggtacagt tcaaagcatg      3240
gaaatggaac ccgccgtctg ctgcaccatg ggcgtgagcg gggagtacgc gactcctgga      3300
cagccgtaac aatgcggatg gcctcaacaa gccaggagcg gcacgaaccc agctcacgag      3360
cgcacagcgt gccaggacgg cggccggcaa ggatgaaatg ttttcctaa tataaatgcg       3420 gactcctgac gcattatatc cattttgcca ctgagccaaa gacacatata tacacgtgcg      3480
ccgccgtcct gcgccacagc cgcctagcgc tccggccgcg cccggttccc tcggcgtcat      3540
gcgctggagc cccctcgcac cctgcaccgc aaagcccatc aacaccacac tcgtccccac      3600
accgcgagtc accgccactg cactcgctgt ccctcaaccc gtcacaatct cgccgacacg      3660
cgataacgaa cccacgcagg tacggcttcc acaaggagcc gtctggcggc accgaccccg      3720
agggcagccg caaggcgcgc ctgctgcaga tctttggcca ctggaacgac aacgtggtgg      3780
acctgatcaa ggccacgccc gaggaggacg tgctgcgccg cgacatcttt gacaggtacg      3840
gaaaagggga gagcggggtg gctggagggc gggaaagggc gaaggggcgg agaaagaaat      3900
gactagggga tggtgttcat ttgtgggatt gagaggggtc cgcggatccc ggcagagggc      3960
gccagtggca aggcgtggga gtcgcggggc ggacaatgct gggccagggg cgcctagtca      4020
ccccgggaca ctgtctcagt atgccgccgt cccggccgcg ccgcacaggc cgcccatctt      4080
cacctggagc aagggccgcg tggccctgct gggcgacagc gcgcacgcca tgcagcccaa      4140
cctgggccag ggcggctgca tggccattga ggacgcctac gagctggcca tcgacctcag      4200
ccgcgccgtg tccgacaagg ccggaaacgc ggcggcggtg gacgtggagg gcgtgctgcg      4260
cagctaccag gacagccgca ttttgcgcgt cagcgccatt cacggcatgg cgggtgagag      4320
ctgcaaccag cgtagtcggg ctgggctgct gtgggcaggg tcgggttggg ttgggcgcac      4380
gtgggcggcg agtgtatgtg cagtgtgacg tgcacactat cataatactt tatgctcacc      4440
gcaccgcgcc gcgccgcacc acgcgccaca ggcatggctg ccttcatggc cagcacctac      4500
aagtgctacc tgggcgaggg ctggagcaag tgggttgagg ggctgcgcat cccgcacccc      4560
ggccgcgtgg tggggcggct ggtgatgctg ctcaccatgc ccagcgtgct ggagtgggtg      4620
ctgggcggca acaccgacca cgtggcgccg caccgcacca gctactgctc gctgggcgac      4680
aagcccaagg tgagcggctg ccgggctggg gggggtgga gggagaggag gaggattgcg       4740
gggagacgag ggagggcaag gcaggcgctg ccttcgtgga tgcaccgccc cgtcgttagc      4800
aggacctcag gaactcgtcc ccaaaaccac aacagaaccc ccaatatcgc ctcttccttc      4860
actgcttgtc acgcctggtc cgccgaccgc aggctttccc cgagagccgc ttccccgagt      4920
tcatgaacaa cgacgcctcc atcatccgct cctcccacgc cgactggctg ctggtggcgg      4980
agcgcgacgc cgccacggcc gccgccgcca acgtgaacgc cgccaccggc agcagcgccg      5040
ccgcggccgc cgccgccgac gtgaacagca gctgccagtg caagggcatc tacatgcgg       5100 actcggcggc cctggtgggc cgctgcgcg ccacctcgcg ccccgcgctg ccgtggacg        5160 acgtgcacgt cgccgagagt cacgcgcagg tctggcgcgg cctcgccggc ctcccccct      5220 cctcgtcgtc cgcctccacc gccgcgcct ctgcgtccgc cgcctcctct gccgccagcg       5280
gcaccgccag caccctgggc agctcggagg gctactggct ccgcgacctg gcagcggcc      5340 gcggcacctg ggtcaacggc aagcgcctgc ccgacggcgc cacggtgcag ctgtggcccg      5400
gcgacgcggg ggagttcggc cggcacccca gccacgaggt gttcaaggtg aagatgcagc      5460
acgtgacgct gcgcagcgac gagctcagcg gccaggccta caccacgctc atggtgggca      5520
```

```
agatccggaa caacgactac gtcatgcccg agtcgcggcc ggacggcggc agccagcagc    5580
cgggccgcct ggtgacggct taagcggcgc cgtgcgtaag ggccggctta cggggggcgg    5640
agtgtcgctg tggagggatg gtctggggtg ggaggaatgg gaggagagcg gcgggagccc    5700
gaggagcgga gcgctggagg cttgcggagc ggcagcttgg gaagagctgc ggagagagga    5760
aggagcgcag ggcgcttgga gcacgcgcca gattacgatc acggcagcgc gaggcgcgcg    5820
tctgacttcg aagtggtaag gaagatttca tgtatgattg cgtcgaggga caccgcaagt    5880
tttacgcgcg gcggagggag ccttggggca tacaacagta cgagcgggcg ttggtgagaa    5940
ggtggtcact ccgtatgaga agatggttac tccgtacctt cgtgagaagc tgctgcgcac    6000
aagttacgaa cctatctgtg tggagagccc ggtagtatat caggggcgag ggtcatgaac    6060
gcgagtggcg agtctgtgag cgccaatttg ttatgcggca taatttcgca tcggggtatt    6120
acgtctacaa aatgttgagc tggcttagcg caggaggcaa cacctcaggc agaatgtacg    6180
aatgtgtgca gaagggcaga gtcaaggcag aggcggagaa gttgtcaggg ctgtgtgtgg    6240
tttggtcagg gcgtggctag atggatatga gacccgccgc cgtctccaga ttgtggcgga    6300
ggtggaactc tcggcccccg cgccagtccc cgcggccagc gcatcccgcc atgcgggttg    6360
ttggctggtg catcgcgcgg ggtgtgctat gagtgtggaa acactatgtc gcgtgtcgtg    6420
ctgaggtctt ttgagaggtt tcgtcgtttg tgcatgtcct gtcccggttg gagtttgagc    6480
gaggtggttc aaagttttg gatcgcgtgg gagagactga aacggtttgg tgagaatggt    6540
tgagacagag gttgggcttg gaaactggag gagaggagca gcgtaactcg aggacgatgc    6600
agtagatgca ccacaacagt tgtggtgggc gcctggagta acacgcgtgc caccaacacg    6660
caattacaga gatccgtcat acaggaggga tcatatgcga tttaattttg gttttgcatt    6720
tgtaagacgt tttcaca                                                  6737
```

<210> SEQ ID NO 6
<211> LENGTH: 6694
<212> TYPE: DNA
<213> ORGANISM: Artificial Sequence
<220> FEATURE:
<223> OTHER INFORMATION: Synthetic sequence, ZEP mutant 3

<400> SEQUENCE: 6

```
gcgacgcacg gctgggccaa attcgccaac ggcaggagac caaatcgatc gaggcgatct      60
tgcgaagttc tcggacaaat cgatcgcacc catagtgatt taagcattac atttgcccaa     120
ggcgtgagaa gtgcgaggcc cgaacggcta tgacgccaat gcgcagctta cgacatttaa     180
agcaaattat tcatacatca tacagcacgc ttatgtgaag aaagccagga ttttaggctc     240
tcgccccgat caagacgatc tccccattgc gaagttctcg gtttctttcc ggttcgcctg     300
ctccgtatga tttaccttg cgctacaaca gcgacttaaa cgacctacgt cgccttactg     360
tgtgcgcgta cgtgtttgta gctgtgagat agttttgtcc gcagcgtacc cgcaaataga     420
atgctcgcga gcacttacac gccctgtggc gttcgccagg tggcaggccg cacggttgca     480
gtgcccagca gcttggtcgc gccagtggca gtcgctcggt cgctgggtt ggcgccctac     540 gtccctgtat gtgagccttc tcggcgcgtt ccggcctgcc agcagcctag cgggcgtcgt     600
catgttcaga ctgctgccac tctccgtgcc gacaacccca gctcggtcgc gcagctggtg     660
catcagaatg gaaaggggat gaaggttatt atcgccggcg cgggcatcgg cggcctggtg     720
ctagccgttg cacttctgaa gcagggcttc caggttcagg tctttgagcg cgacctgacg     780
```

```
gccatccgcg gcgagggcaa gtaccgtgga cccatcacag gtgcgttcgc cggaacacca    840
acgcgcttgt ttttgctgtg ccgcgaccat gaactaggcc ttatcttgag gtgttagcat    900
gtttagccag cgttggatct gtgtggcgag gttggggtga gaacccttcc tgtgtacctg    960
ctcgggcgta ccttgtgccc caccgctgac tggcttactt aatgacaaaa cgcaggttca   1020
aagcaatgcg ctcgctgcgc tggaggctat cgatcccgag gtggccgcgg aggtgctgcg   1080
cgagggctgc atcactggcg accgtatcaa cgggctctgc gacggcctga ctggcgagtg   1140
gtgagtaggc aatccagctg tgcatccagt cgcgcggttg cggaggtcgt ctcgggaaac   1200
gcgacgtggc gtccactcgc ccaaggagtg gtctcccgca gcgtggtctc ccgcagctcg   1260
ggtgcaacac cctgccccct gccgcgagcg cgctgcgctt gcttatgttg cgcagcggtg   1320
tgagttacaa cagcttctgt tgaagagctg tcatacgaag cacggcgcgc tgtggcgctg   1380
cagccgtgct gtggaaactc caacacctcc accgccagcc tgcgcacgca cacgcaatac   1440
actcgcctcg tgtgccccct cctcacacaa cggcatgtga cactcagttt taactcttat   1500
tttgacagct gagagctaca cgcttgggtg aatgggaggg tccttgatgt ttcgttgcac   1560
tccgtggctc cggagtccgt gcggaccgtc acccacaaat gggagcgcac ggctttcttg   1620
tgctgtctgc cccgttagcc actaactgcg aatgaccttg acagtttact ttgctatttt   1680
tccttccagg tacgtcaagt tcgacacgtt ccacccggcg gtcagcaagg gcctgccggt   1740
gacccgcgtc atcagccgcc tcacgctgca gcagatcctg gccaaagccg tggagcggtg   1800
agccgtgcgc gcggtgtgat ggctttagcg tcagtgctag catgggggtt ggtgggtggt   1860
aatcgcggcg cccatggccg ggtagcagcg gccgaaagct ggcgcagagc gcgcgttgga   1920
caagcggtcc tgttgccggt atgggcacga gcagggcgct ggtgcgggca aagggcagag   1980
tggagttgca gagcagcgct ggcgtcggct gtgcgctctc caaatggcct cgtggcattc   2040
tgacgggaca catcctggaa aatagtagcg cacccaactg ctggtggctc ctcgtacaat   2100
cccccccaatt tacaatcgct cgttctggct cgcagctacg gcggcccgg caccatccag   2160
aacggctgca acgtgaccga gttcacggag cgccgcaacg acaccaccgg caacaacgag   2220
gtgagagcgt gctaagaaga gcatgcacgt ggagcgtgta aaattgtgtg gcctgaagcg   2280
gcagtgcctg cggcatggac taggtggttg cagcatgctg cgcgcgtggg ttgccggtca   2340
ggaaaccgcc ggaccgagcc gcgcagattc agtcaggagc ggattaggaa gtttgaaaaa   2400
cagggttcgg agtgtgcaag cgggctcagg agctgtggtg ccttcctaca ccggtcgccc   2460
taccaggcac ccactgaaac tgtaaaaccg ttgctgcgcc ggcgatgccc tctacttcac   2520
taggtgactg tgcagctgga ggacgggcgc acgtttgcgg ccgacgtgct ggtgggcgcc   2580
gacggcatct ggtccaagat ccgtaagcag ctcattggcg agaccaaggc caactacagc   2640
gggtacacct gctacaccgg tgagattatt gaccttcaag ttggaaggag ggagcggggg   2700
gagcggaatg gaaggaagca gcgtggacgg ggcgcacgga ggggagggga ctgcgggtca   2760
tagcgccgcc ttgcggggcg tgaggagtgt tgggcggata ttcagttttc tttgcccaag   2820
atcttcccac aatccgcgtg tgtctgacgc gggatgtggc ccctgctgcc atggcttcgc   2880
aggcatctcg gactttacgc cggcggacat tgacattgtg gctaccgcg tgttcctggg    2940
caacggccag tactttgtca gcagcgacgt gggcaacggc aagatgcagt ggtgagcggc   3000
ggcgggcggg cgagcgaggg ctgcggggtc tgagggtgt gtaccgggcg gaagggaggg    3060
gaagggaggg gaagggaagg caggatgcag gcgagggcag gatgtgatgg tgggaagagg   3120
gcgtggcgag cagcaactgg aaaggtggtg ggtaaaaaaa tggtccatga atatggctcg   3180
```

```
gtacagttca aagcatggaa atggaacccg ccgtctgctg caccatgggc gtgagcgggg    3240
agtacgcgac tcctggacag ccgtaacaat gcggatggcc tcaacaagcc aggagcggca    3300
cgaacccagc tcacgagcgc acagcgtgcc aggacggcgg ccggcaagga tgaaatgttt    3360
ttcctaatat aaatgcggac tcctgacgca ttatatccat tttgccactg agccaaagac    3420
acatatatac acgtgcgccg ccgtcctgcg ccacagccgc ctagcgctcc ggccgcgccc    3480
ggttccctcg gcgtcatgcg ctggagcccc ctcgcaccct gcaccgcaaa gcccatcaac    3540
accacactcg tccccacacc gcgagtcacc gccactgcac tcgctgtccc tcaacccgtc    3600
acaatctcgc cgacacgcga taacgaaccc acgcaggtac ggcttccaca aggagccgtc    3660
tggcggcacc gaccccgagg gcagccgcaa ggcgcgcctg ctgcagatct ttggccactg    3720
gaacgacaac gtggtggacc tgatcaaggc cacgcccgag gaggacgtgc tgcgccgcga    3780
catctttgac aggtacggaa aaagggagag cggggtggct ggagggcggg aaagggcgaa    3840
ggggcggaga aagaaatgac tagggatgg tgttcatttg tgggattgag aggggtccgc    3900
ggatcccggc agagggcgcc agtggcaagg cgtgggagtc gcggggcgga caatgctggg    3960
ccaggggcgc ctagtcaccc cgggacactg tctcagtatg ccgccgtccc ggccgcgccg    4020
cacaggccgc ccatcttcac ctggagcaag ggccgcgtgg ccctgctggg cgacagcgcg    4080
cacgccatgc agcccaacct gggccagggc ggctgcatgg ccattgagga cgcctacgag    4140
ctggccatcg acctcagccg cgccgtgtcc gacaaggccg aaacgcggc ggcggtggac    4200 gtggagggcg tgctgcgcag ctaccaggac agccgcattt tgcgcgtcag cgccattcac    4260
ggcatggcgg gtgagagctg caaccagcgt agtcgggctg ggctgctgtg gcagggtcg    4320 ggttgggttg gcgcacgtg ggcggcgagt gtatgtgcag tgtgacgtgc acactatcat    4380
aatactttat gctcaccgca ccgcgccgcg ccgcaccacg cgccacaggc atggctgcct    4440
tcatggccag cacctacaag tgctacctgg gcgagggctg gagcaagtgg gttgaggggc    4500
tgcgcatccc gcacccccggc cgcgtggtgg ggcggctggt gatgctgctc accatgccca    4560
gcgtgctgga gtgggtgctg gcggcaaca ccgaccacgt ggcgccgcac cgcaccagct    4620
actgctcgct gggcgacaag cccaaggtga gcggctgccg gctgggggg gggtggaggg    4680 agaggaggag gattgcgggg agacgaggga gggcaaggca ggcgctgcct tcgtggatgc    4740
accgccccgt cgttagcagg acctcaggaa ctcgtccca aaaccacaac agaaccccca    4800
atatcgcctc ttccttcact gcttgtcacg cctggtccgc cgaccgcagg cttttccccga    4860 gagccgcttc cccgagttca tgaacaacga cgcctccatc atccgctcct cccacgccga    4920
ctggctgctg gtggcggagc gcgacgccgc cacggccgcc gccgccaacg tgaacgccgc    4980
caccggcagc agcgccgccg cggccgccgc cgccgacgtg aacagcagct gccagtgcaa    5040
gggcatctac atggcggact cggcggccct ggtgggccgc tgcggcgcca cctcgcgccc    5100
cgcgctggcc gtgacgacg tgcacgtcgc cgagagtcac gcgcaggtct ggcgcggcct    5160
cgccggcctc ccccctcct cgtcgtccgc ctccaccgcc gccgcctctg cgtccgccgc    5220
ctcctctgcc gccagcggca ccgccagcac cctgggcagc tcggagggct actggctccg    5280
cgacctgggc agcggccgcg gcacctgggt caacggcaag cgcctgcccg acggcgccac    5340
ggtgcagctg tggcccggcg acgcggtgga gttcggccgg caccccagcc acgaggtgtt    5400
caaggtgaag atgcagcacg tgacgctgcg cagcgacgag ctcagcggcc aggcctacac    5460
cacgctcatg gtgggcaaga tccggaacaa cgactacgtc atgcccgagt cgcggccgga    5520
```

-continued

| | |
|---|---|
| cggcggcagc cagcagccgg gccgcctggt gacggcttaa gcggcgccgt gcgtaagggc | 5580 |
| cggcttacgg gggcggcagt gtcgctgtgg agggatggtc tggggtggga ggaatgggag | 5640 |
| gagagcggcg ggagcccgag gagcggagcg ctggaggctt gcggagcggc agcttgggaa | 5700 |
| gagctgcgga gagaggaagg agcgcagggc gcttggagca cgcgccagat tacgatcacg | 5760 |
| gcagcgcgag gcgcgcgtct gacttcgaag tggtaaggaa gatttcatgt atgattgcgt | 5820 |
| cgagggacac cgcaagtttt acgcgcggcg gaggagcct tggggcatac aacagtacga | 5880 |
| gcgggcgttg gtgagaaggt ggtcactccg tatgagaaga tggttactcc gtaccttcgt | 5940 |
| gagaagctgc tgcgcacaag ttacgaacct atctgtgtgg agagcccggt agtatatcag | 6000 |
| gggcgagggt catgaacgcg agtggcgagt ctgtgagcgc caatttgtta tgcggcataa | 6060 |
| tttcgcatcg gggtattacg tctacaaaat gttgagctgg cttagcgcag gaggcaacac | 6120 |
| ctcaggcaga atgtacgaat gtgtgcagaa gggcagagtc aaggcagagg cggagaagtt | 6180 |
| gtcagggctg tgtgtggttt ggtcagggcg tggctagatg gatatgagac ccgccgccgt | 6240 |
| ctccagattg tggcggaggt ggaactctcg gcccccgcgc cagtccccgc ggccagcgca | 6300 |
| tcccgccatg cggggttgttg gctggtgcat cgcgcggggt gtgctatgag tgtgaaaca | 6360 |
| ctatgtcgcg tgtcgtgctg aggtctgttg agaggtttcg tcgtttgtgc atgtcctgtc | 6420 |
| ccggttggag tttgagcgag gtggttcaaa gttttttggat cgcgtgggag agactgaaac | 6480 |
| ggtttggtga gaatggttga gacagaggtt gggcttggaa actggaggag aggagcagcg | 6540 |
| taactcgagg acgatgcagt agatgcacca caacagttgt ggtgggcgcc tggagtaaca | 6600 |
| cgcgtgccac caacacgcaa ttacagagat ccgtcataca ggagggatca tatgcgattt | 6660 |
| aattttggtt ttgcatttgt aagacgtttt caca | 6694 |

<210> SEQ ID NO 7
<211> LENGTH: 23
<212> TYPE: DNA
<213> ORGANISM: Chlamydomonas reinhardtii

<400> SEQUENCE: 7

| | |
|---|---|
| cccatccagg tgcgttcgcc gga | 23 |

<210> SEQ ID NO 8
<211> LENGTH: 96
<212> TYPE: RNA
<213> ORGANISM: Artificial Sequence
<220> FEATURE:
<223> OTHER INFORMATION: gRNA

<400> SEQUENCE: 8

| | |
|---|---|
| uccggcgaac gcaccuggau guuuuagagc uagaaauagc aaguuaaaau aaggcuaguc | 60 |
| cguuaucaac uugaaaaagu ggcaccgagu cggugc | 96 |

<210> SEQ ID NO 9
<211> LENGTH: 1406
<212> TYPE: PRT
<213> ORGANISM: Chlamydomonas reinhardtii

<400> SEQUENCE: 9

Met Gly Ser Ser His His His His His His Val Tyr Pro Tyr Asp Val
1               5                   10                  15

Pro Asp Tyr Ala Glu Leu Pro Pro Lys Lys Lys Arg Lys Val Gly Ile
            20                  25                  30

```
Arg Ile Pro Gly Glu Lys Pro Asp Lys Lys Tyr Ser Ile Gly Leu Asp
             35                  40                  45
Ile Gly Thr Asn Ser Val Gly Trp Ala Val Ile Thr Asp Glu Tyr Lys
 50                  55                  60
Val Pro Ser Lys Lys Phe Lys Val Leu Gly Asn Thr Asp Arg His Ser
 65                  70                  75                  80
Ile Lys Lys Asn Leu Ile Gly Ala Leu Leu Phe Asp Ser Gly Glu Thr
                 85                  90                  95
Ala Glu Ala Thr Arg Leu Lys Arg Thr Ala Arg Arg Tyr Thr Arg
                100                 105                 110
Arg Lys Asn Arg Ile Cys Tyr Leu Gln Glu Ile Phe Ser Asn Glu Met
            115                 120                 125
Ala Lys Val Asp Asp Ser Phe Phe His Arg Leu Glu Glu Ser Phe Leu
130                 135                 140
Val Glu Glu Asp Lys Lys His Glu Arg His Pro Ile Phe Gly Asn Ile
145                 150                 155                 160
Val Asp Glu Val Ala Tyr His Glu Lys Tyr Pro Thr Ile Tyr His Leu
                165                 170                 175
Arg Lys Lys Leu Val Asp Ser Thr Asp Lys Ala Asp Leu Arg Leu Ile
            180                 185                 190
Tyr Leu Ala Leu Ala His Met Ile Lys Phe Arg Gly His Phe Leu Ile
        195                 200                 205
Glu Gly Asp Leu Asn Pro Asp Asn Ser Asp Val Asp Lys Leu Phe Ile
    210                 215                 220
Gln Leu Val Gln Thr Tyr Asn Gln Leu Phe Glu Glu Asn Pro Ile Asn
225                 230                 235                 240
Ala Ser Gly Val Asp Ala Lys Ala Ile Leu Ser Ala Arg Leu Ser Lys
                245                 250                 255
Ser Arg Arg Leu Glu Asn Leu Ile Ala Gln Leu Pro Gly Glu Lys Lys
            260                 265                 270
Asn Gly Leu Phe Gly Asn Leu Ile Ala Leu Ser Leu Gly Leu Thr Pro
        275                 280                 285
Asn Phe Lys Ser Asn Phe Asp Leu Ala Glu Asp Ala Lys Leu Gln Leu
    290                 295                 300
Ser Lys Asp Thr Tyr Asp Asp Asp Leu Asp Asn Leu Leu Ala Gln Ile
305                 310                 315                 320
Gly Asp Gln Tyr Ala Asp Leu Phe Leu Ala Ala Lys Asn Leu Ser Asp
                325                 330                 335
Ala Ile Leu Leu Ser Asp Ile Leu Arg Val Asn Thr Glu Ile Thr Lys
            340                 345                 350
Ala Pro Leu Ser Ala Ser Met Ile Lys Arg Tyr Asp Glu His His Gln
        355                 360                 365
Asp Leu Thr Leu Leu Lys Ala Leu Val Arg Gln Gln Leu Pro Glu Lys
    370                 375                 380
Tyr Lys Glu Ile Phe Phe Asp Gln Ser Lys Asn Gly Tyr Ala Gly Tyr
385                 390                 395                 400
Ile Asp Gly Gly Ala Ser Gln Glu Glu Phe Tyr Lys Phe Ile Lys Pro
                405                 410                 415
Ile Leu Glu Lys Met Asp Gly Thr Glu Glu Leu Leu Val Lys Leu Asn
            420                 425                 430
Arg Glu Asp Leu Leu Arg Lys Gln Arg Thr Phe Asp Asn Gly Ser Ile
        435                 440                 445
```

```
Pro His Gln Ile His Leu Gly Glu Leu His Ala Ile Leu Arg Arg Gln
    450                 455                 460
Glu Asp Phe Tyr Pro Phe Leu Lys Asp Asn Arg Glu Lys Ile Glu Lys
465                 470                 475                 480
Ile Leu Thr Phe Arg Ile Pro Tyr Tyr Val Gly Pro Leu Ala Arg Gly
                485                 490                 495
Asn Ser Arg Phe Ala Trp Met Thr Arg Lys Ser Glu Glu Thr Ile Thr
            500                 505                 510
Pro Trp Asn Phe Glu Glu Val Val Asp Lys Gly Ala Ser Ala Gln Ser
        515                 520                 525
Phe Ile Glu Arg Met Thr Asn Phe Asp Lys Asn Leu Pro Asn Glu Lys
530                 535                 540
Val Leu Pro Lys His Ser Leu Leu Tyr Glu Tyr Phe Thr Val Tyr Asn
545                 550                 555                 560
Glu Leu Thr Lys Val Lys Tyr Val Thr Glu Gly Met Arg Lys Pro Ala
                565                 570                 575
Phe Leu Ser Gly Glu Gln Lys Lys Ala Ile Val Asp Leu Leu Phe Lys
            580                 585                 590
Thr Asn Arg Lys Val Thr Val Lys Gln Leu Lys Glu Asp Tyr Phe Lys
        595                 600                 605
Lys Ile Glu Cys Phe Asp Ser Val Glu Ile Ser Gly Val Glu Asp Arg
610                 615                 620
Phe Asn Ala Ser Leu Gly Thr Tyr His Asp Leu Leu Lys Ile Ile Lys
625                 630                 635                 640
Asp Lys Asp Phe Leu Asp Asn Glu Glu Asn Glu Asp Ile Leu Glu Asp
                645                 650                 655
Ile Val Leu Thr Leu Thr Leu Phe Glu Asp Arg Glu Met Ile Glu Glu
            660                 665                 670
Arg Leu Lys Thr Tyr Ala His Leu Phe Asp Asp Lys Val Met Lys Gln
        675                 680                 685
Leu Lys Arg Arg Arg Tyr Thr Gly Trp Gly Arg Leu Ser Arg Lys Leu
690                 695                 700
Ile Asn Gly Ile Arg Asp Lys Gln Ser Gly Lys Thr Ile Leu Asp Phe
705                 710                 715                 720
Leu Lys Ser Asp Gly Phe Ala Asn Arg Asn Phe Met Gln Leu Ile His
                725                 730                 735
Asp Asp Ser Leu Thr Phe Lys Glu Asp Ile Gln Lys Ala Gln Val Ser
            740                 745                 750
Gly Gln Gly Asp Ser Leu His Glu His Ile Ala Asn Leu Ala Gly Ser
        755                 760                 765
Pro Ala Ile Lys Lys Gly Ile Leu Gln Thr Val Lys Val Val Asp Glu
770                 775                 780
Leu Val Lys Val Met Gly Arg His Lys Pro Glu Asn Ile Val Ile Glu
785                 790                 795                 800
Met Ala Arg Glu Asn Gln Thr Thr Gln Lys Gly Gln Lys Asn Ser Arg
                805                 810                 815
Glu Arg Met Lys Arg Ile Glu Glu Gly Ile Lys Glu Leu Gly Ser Gln
            820                 825                 830
Ile Leu Lys Glu His Pro Val Glu Asn Thr Gln Leu Gln Asn Glu Lys
        835                 840                 845
Leu Tyr Leu Tyr Tyr Leu Gln Asn Gly Arg Asp Met Tyr Val Asp Gln
850                 855                 860
```

```
Glu Leu Asp Ile Asn Arg Leu Ser Asp Tyr Asp Val Asp His Ile Val
865                 870                 875                 880

Pro Gln Ser Phe Leu Lys Asp Asp Ser Ile Asp Asn Lys Val Leu Thr
            885                 890                 895

Arg Ser Asp Lys Asn Arg Gly Lys Ser Asp Asn Val Pro Ser Glu Glu
        900                 905                 910

Val Val Lys Lys Met Lys Asn Tyr Trp Arg Gln Leu Leu Asn Ala Lys
        915                 920                 925

Leu Ile Thr Gln Arg Lys Phe Asp Asn Leu Thr Lys Ala Glu Arg Gly
930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
                965                 970                 975

Met Asn Thr Lys Tyr Asp Glu Asn Asp Lys Leu Ile Arg Glu Val Lys
                980                 985                 990

Val Ile Thr Leu Lys Ser Lys Leu Val Ser Asp Phe Arg Lys Asp Phe
            995                 1000                1005

Gln Phe Tyr Lys Val Arg Glu Ile Asn Asn Tyr His His Ala His
    1010                1015                1020

Asp Ala Tyr Leu Asn Ala Val Val Gly Thr Ala Leu Ile Lys Lys
    1025                1030                1035

Tyr Pro Lys Leu Glu Ser Glu Phe Val Tyr Gly Asp Tyr Lys Val
    1040                1045                1050

Tyr Asp Val Arg Lys Met Ile Ala Lys Ser Glu Gln Glu Ile Gly
    1055                1060                1065

Lys Ala Thr Ala Lys Tyr Phe Phe Tyr Ser Asn Ile Met Asn Phe
    1070                1075                1080

Phe Lys Thr Glu Ile Thr Leu Ala Asn Gly Glu Ile Arg Lys Arg
    1085                1090                1095

Pro Leu Ile Glu Thr Asn Gly Glu Thr Gly Glu Ile Val Trp Asp
    1100                1105                1110

Lys Gly Arg Asp Phe Ala Thr Val Arg Lys Val Leu Ser Met Pro
    1115                1120                1125

Gln Val Asn Ile Val Lys Lys Thr Glu Val Gln Thr Gly Gly Phe
    1130                1135                1140

Ser Lys Glu Ser Ile Leu Pro Lys Arg Asn Ser Asp Lys Leu Ile
    1145                1150                1155

Ala Arg Lys Lys Asp Trp Asp Pro Lys Lys Tyr Gly Gly Phe Asp
    1160                1165                1170

Ser Pro Thr Val Ala Tyr Ser Val Leu Val Val Ala Lys Val Glu
    1175                1180                1185

Lys Gly Lys Ser Lys Lys Leu Lys Ser Val Lys Glu Leu Leu Gly
    1190                1195                1200

Ile Thr Ile Met Glu Arg Ser Ser Phe Glu Lys Asn Pro Ile Asp
    1205                1210                1215

Phe Leu Glu Ala Lys Gly Tyr Lys Glu Val Lys Lys Asp Leu Ile
    1220                1225                1230

Ile Lys Leu Pro Lys Tyr Ser Leu Phe Glu Leu Glu Asn Gly Arg
    1235                1240                1245

Lys Arg Met Leu Ala Ser Ala Gly Glu Leu Gln Lys Gly Asn Glu
    1250                1255                1260
```

| | | | | | | | | | | |
|---|---|---|---|---|---|---|---|---|---|---|
| Leu | Ala | Leu | Pro | Ser | Lys | Tyr | Val | Asn | Phe | Leu | Tyr | Leu | Ala | Ser |
| | 1265 | | | | 1270 | | | | 1275 | |

Leu Ala Leu Pro Ser Lys Tyr Val Asn Phe Leu Tyr Leu Ala Ser
    1265                1270                1275

His Tyr Glu Lys Leu Lys Gly Ser Pro Glu Asp Asn Glu Gln Lys
    1280                1285                1290

Gln Leu Phe Val Glu Gln His Lys His Tyr Leu Asp Glu Ile Ile
    1295                1300                1305

Glu Gln Ile Ser Glu Phe Ser Lys Arg Val Ile Leu Ala Asp Ala
    1310                1315                1320

Asn Leu Asp Lys Val Leu Ser Ala Tyr Asn Lys His Arg Asp Lys
    1325                1330                1335

Pro Ile Arg Glu Gln Ala Glu Asn Ile Ile His Leu Phe Thr Leu
    1340                1345                1350

Thr Asn Leu Gly Ala Pro Ala Ala Phe Lys Tyr Phe Asp Thr Thr
    1355                1360                1365

Ile Asp Arg Lys Arg Tyr Thr Ser Thr Lys Glu Val Leu Asp Ala
    1370                1375                1380

Thr Leu Ile His Gln Ser Ile Thr Gly Leu Tyr Glu Thr Arg Ile
    1385                1390                1395

Asp Leu Ser Gln Leu Gly Gly Asp
    1400                1405

<210> SEQ ID NO 10
<211> LENGTH: 76
<212> TYPE: DNA
<213> ORGANISM: Artificial Sequence
<220> FEATURE:
<223> OTHER INFORMATION: Synthetic sequence

<400> SEQUENCE: 10
gttttagagc tagaaatagc aagttaaaat aaggctagtc cgttatcaac ttgaaaaagt    60
ggcaccgagt cggtgc                                                    76

<210> SEQ ID NO 11
<211> LENGTH: 23
<212> TYPE: DNA
<213> ORGANISM: Artificial Sequence
<220> FEATURE:
<223> OTHER INFORMATION: Synthetic sequence

<400> SEQUENCE: 11
tccggcgaac gcacctggat ggg                                            23

<210> SEQ ID NO 12
<211> LENGTH: 23
<212> TYPE: DNA
<213> ORGANISM: Artificial Sequence
<220> FEATURE:
<223> OTHER INFORMATION: Synthetic sequence

<400> SEQUENCE: 12
caccagctgc gcgaccgagc tgg                                            23

<210> SEQ ID NO 13
<211> LENGTH: 23
<212> TYPE: DNA
<213> ORGANISM: Artificial Sequence
<220> FEATURE:
<223> OTHER INFORMATION: Synthetic sequence

<400> SEQUENCE: 13
gccgttgcac ttctgaagca ggg                                            23

```
<210> SEQ ID NO 14
<211> LENGTH: 23
<212> TYPE: DNA
<213> ORGANISM: Artificial Sequence
<220> FEATURE:
<223> OTHER INFORMATION: Synthetic sequence

<400> SEQUENCE: 14
tccggcgaac gcacctggat ggg                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic sequence

<400> SEQUENCE: 15
tggtgggcgc cgacggcatc tgg                                              23

<210> SEQ ID NO 16
<211> LENGTH: 23
<212> TYPE: DNA
<213> ORGANISM: Artificial Sequence
<220> FEATURE:
<223> OTHER INFORMATION: Synthetic sequence

<400> SEQUENCE: 16
ccatggcttc gcaggcatct cgg                                              23

<210> SEQ ID NO 17
<211> LENGTH: 83
<212> TYPE: DNA
<213> ORGANISM: Artificial Sequence
<220> FEATURE:
<223> OTHER INFORMATION: Synthetic sequence

<400> SEQUENCE: 17
gccatccgcg gcgagggcaa gtaccgtgga cccatccagg tgcgttcgcc ggaacaccaa      60
cgcgcttgtt tttgctgtgc cgc                                              83

<210> SEQ ID NO 18
<211> LENGTH: 85
<212> TYPE: DNA
<213> ORGANISM: Artificial Sequence
<220> FEATURE:
<223> OTHER INFORMATION: Synthetic sequence

<400> SEQUENCE: 18
gccatccgcg gcgagggcaa gtaccgtgga cccatctcca ggtgcgttcg ccggaacacc      60
aacgcgcttg tttttgctgt gccgc                                            85

<210> SEQ ID NO 19
<211> LENGTH: 82
<212> TYPE: DNA
<213> ORGANISM: Artificial Sequence
<220> FEATURE:
<223> OTHER INFORMATION: Synthetic sequence

<400> SEQUENCE: 19
gccatccgcg gcgagggcaa gtaccgtgga cccatcaggt gcgttcgccg gaacaccaac      60
gcgcttgttt tgctgtgcc gc                                                82
```

```
<210> SEQ ID NO 20
<211> LENGTH: 79
<212> TYPE: DNA
<213> ORGANISM: Artificial Sequence
<220> FEATURE:
<223> OTHER INFORMATION: Synthetic sequence

<400> SEQUENCE: 20
gccatccgcg gcgagggcaa gtaccgtgga cccaggtgcg ttcgccggaa caccaacgcg      60
cttgtttttg ctgtgccgc                                                   79

<210> SEQ ID NO 21
<211> LENGTH: 89
<212> TYPE: DNA
<213> ORGANISM: Artificial Sequence
<220> FEATURE:
<223> OTHER INFORMATION: Synthetic sequence

<400> SEQUENCE: 21
gccatccgcg gcgagggcaa gtaccgtgga cccatcaaca tccaggtgcg ttcgccggaa      60
caccaacgcg cttgtttttg ctgtgccgc                                        89

<210> SEQ ID NO 22
<211> LENGTH: 84
<212> TYPE: DNA
<213> ORGANISM: Artificial Sequence
<220> FEATURE:
<223> OTHER INFORMATION: Synthetic sequence

<400> SEQUENCE: 22
gccatccgcg gcgagggcaa gtaccgtgga cccatctcag gtgcgttcgc cggaacacca      60
acgcgcttgt ttttgctgtg ccgc                                             84

<210> SEQ ID NO 23
<211> LENGTH: 12
<212> TYPE: DNA
<213> ORGANISM: Chlamydomonas reinhardtii

<400> SEQUENCE: 23
cccatccagg tg                                                          12

<210> SEQ ID NO 24
<211> LENGTH: 54
<212> TYPE: DNA
<213> ORGANISM: Artificial Sequence
<220> FEATURE:
<223> OTHER INFORMATION: Synthetic sequence

<400> SEQUENCE: 24
cccatcgaaa ttaataagac tcattatatt ccggcgaacg cacctggaca ggtg            54

<210> SEQ ID NO 25
<211> LENGTH: 56
<212> TYPE: DNA
<213> ORGANISM: Artificial Sequence
<220> FEATURE:
<223> OTHER INFORMATION: Synthetic sequence

<400> SEQUENCE: 25
cccatctagc tctaaaacat ccaggtgcgt tcgccggact atagtgagta caggtg          56

<210> SEQ ID NO 26
<211> LENGTH: 13
<212> TYPE: DNA
```

```
<213> ORGANISM: Artificial Sequence
<220> FEATURE:
<223> OTHER INFORMATION: Synthetic sequence

<400> SEQUENCE: 26
cccatcacag gtg                                                        13
```

CHLAMYDOMONAS MUTANTS PRODUCED USING RGEN RNP AND METHOD FOR PREPARING PIGMENT USING THE SAME

CROSS-REFERENCE TO RELATED APPLICATION

This application is a Divisional of U.S. application Ser. No. 16/050,012 filed on Jul. 31, 2018, which is a Continuation-in-Part (CIP) of PCT Application No. PCT/KR2017/004268, filed on Apr. 21, 2017, which claims priority to Korean Patent Application No. 2016-0049439, filed Apr. 22, 2016, and to Korean Patent Application No. 2017-0041761, filed Mar. 31, 2017, and to Korean Patent Application No. 2017-0041762, filed Mar. 31, 2017, the disclosures of which are incorporated herein by reference in their entirety.

TECHNICAL FIELD

The present invention relates to an alga having a pigment producing ability, a dye composition containing the alga, and a method for preparing the pigment.

BACKGROUND ART

Macular degeneration is a disease in which degeneration occurs in the macula which is a nerve tissue located in the center of the inner retina of the eye and causes vision impairment, and since most of the photoreceptors are gathered in the macula and a place where an image of an object is formed is also at the center of the macula, the macula plays a very important role in vision. The most common cause of macular degeneration may be an increase in age (age-related macular degeneration), and is known to be related to family history, race, and smoking. Because the macula is responsible for central vision, if degeneration occurs in the macula, a decrease in vision, central scotoma, metamorphopsia which is a symptom in which things appear distorted, and the like occur. Macular degeneration is largely classified into non-exudative (dry) and exudative (wet), and the non-exudative macular degeneration does not significantly affect vision in most cases, except for the late stage when the atrophy of the retina and the choroid appears, and is a step in which yellow deposits called drusen are seen under the retina, but in the case of the exudative macular degeneration in which subretinal hemorrhage or subretinal fluid, pigment epithelial detachment, and the like appear, when the position of such a lesion is present under the macula or immediately adjacent to the macula, a drop in vision appears from the initial stage. The exudative macular degeneration accounts for about 10 to 20% of the total cases of macular degeneration, but if the exudative macular degeneration is left as it is without being treated, vision rapidly deteriorates, so that many patients will be blind within two years after being diagnosed with the exudative macular degeneration. In order to prevent macular degeneration, it is important to find an abnormality of the macula early through a periodic funduscopic examination and to make an effort so as to reduce the adjustable factors such as obesity, smoking, and hypertension. Since smoking causes damage to choroidal circulation leading to a drop in antioxidant factors in blood and causes choroidal vasoconstriction to cause low oxidative damage, a patient who is at risk of macular degeneration necessarily needs to quit smoking. Further, since a macular pigment (lutein, zeaxanthin) reduces damage caused by aging and serves to maintain a healthy retina, sufficiently ingesting the macular pigment through vegetables and fruits or taking commercialized vitamin supplements can help in the prevention of macular degeneration.

The macular pigment serves to reduce age-related failing eyesight caused in the central part of the retina and prevent retinal tissue damage due to bright light, and representative examples thereof include a xanthophyll as a carotenoid-based oxycarotenoid pigment produced by oxygenation of a carotenoid. Examples of a pigment belonging to xanthophylls include lutein, zeaxanthin, or the like. It is known that lutein acts as an antioxidant that protects the inside of the eyes that is damaged by free oxygen radicals naturally produced in the body, reduces the growth of blood vessels that supply carcinomas to kill cancer cells, and has some effects on prevention of breast cancer, colon cancer, lung cancer, ovarian cancer, and skin cancer.

Animals cannot produce xanthophylls and can obtain xanthophylls only through ingestion of food, but these xanthophylls are present together with chlorophylls and carotenes in the green parts such as leaves, flowers, and fruits of plants. Recently, a health functional food for eye health, including xanthophylls, and the like has attracted attention.

Existing marigold flowers are representative as a raw material for zeaxanthin and lutein, and those extracted from other higher plants has also been studied. In addition, zeaxanthin and lutein are also produced by genetically mutating the pigment synthesis mechanism in bacteria. Studies have also been conducted to obtain these pigments from microalgae. Among these conventional raw materials, marigold flowers have a disadvantage in that it takes a long time to breed flowering plants for production, and have a problem in that the production unit cost is high because the production amount is not large as compared to the land area for production.

In order to solve these problems, the development of zeaxanthin and lutein-producing algae into which a pigment synthesis mechanism is inserted using a bacterial system for replacing a higher plant system was carried out, but there is a problem in that a pigment obtained from bacteria is not suitable for ultimate use as a food additive. In addition, since genetically modified organisms (GMOs) using a genetic insertion technology and the like are not preferred in the domestic market, the GMOs act as a fatal disadvantage in the food additive marker where consumers' perceptions are important, and likewise as in the higher plant system, there is a problem in that a large cost of maintaining a bacterial culture solution, a bioreactor, or the like may be required.

In the case of a method of obtaining these pigments from microalgae, the conventional microalgae are a wild type which is not improved, and have a limitation in being used as optimal producing algae because the content of lutein is constant, but the content of zeaxanthin is very low depending on the amount of light.

REFERENCES OF THE RELATED ART

[Patent Document]
Korean Patent Application No. 2014-7007656

DISCLOSURE

Technical Problem

An object of the present invention is to provide a method capable of replacing a xanthophyll used as a raw material of a conventional food or a method capable of replacing a conventional raw material production method, and specifically to provide a microorganism having an excellent ability to produce xanthophylls, particularly, lutein and zaexanthin, a composition including the same, and a method for preparing xanthophylls using the same.

Technical Solution

In order to achieve the aforementioned object, the present inventors have made efforts to develop algae capable of solving the insufficient productivity of wild-type or conventionally present microalgae by using other mutations without a genetic recombination method which may be a problem in the food industry, and as a result, developed a mutant having a higher yield of macular pigment than a conventional *Chlamydomonas reinhardtii* alga and identified an optimal method for preparing a pigment using the same, thereby completing the present invention.

In this regard, the present invention provides a *Chlamydomonas reinhardtii* mutant having a ZEP gene mutation in which a base sequence represented by SEQ ID NO: 2 is inserted between a 816th base and a 817th base in a ZEP gene sequence of a *Chlamydomonas reinhardtii* cw15 WT represented by SEQ ID NO: 1 and having an ability to produce xanthophylls.

Further, the present invention provides a *Chlamydomonas reinhardtii* mutant having a ZEP gene mutation in which a base sequence represented by SEQ ID NO: 4 is inserted between a 816th base and a 817th base in a ZEP gene sequence of a *Chlamydomonas reinhardtii* cw15 WT represented by SEQ ID NO: 1 and having an ability to produce xanthophylls.

In addition, the present invention provides a *Chlamydomonas reinhardtii* mutant having a ZEP gene mutation in which a base A is inserted between a 816th base and a 817th base in a ZEP gene sequence of a *Chlamydomonas reinhardtii* cw15 WT represented by SEQ ID NO: 1 and having an ability to produce xanthophylls.

The three *Chlamydomonas reinhardtii* mutants may each have an ability to produce xanthophylls.

The three *Chlamydomonas reinhardtii* mutants may each have an ability to produce one or more pigments selected from the group consisting of lutein and zeaxanthin; and chlorophyll b, chlorophyll a, and β-carotene.

Furthermore, the present invention provides a culture of the *Chlamydomonas reinhardtii* mutant.

Further, the present invention provides a pigment composition including one or more selected from the group consisting of a culture of the mutant, a dry material thereof, and an extract thereof.

In addition, the present invention provides a composition for oral administration, including one or more selected from the group consisting of a culture of the mutant, a dry material thereof, and an extract thereof.

Furthermore, the present invention provides a composition for feed or a feed additive, including one or more selected from the group consisting of a culture of the mutant, a dry material thereof, and an extract thereof.

Further, the present invention provides a composition for a food or food additive, including one or more selected from the group consisting of a culture of the mutant, a dry material thereof, and an extract thereof.

In addition, the present invention provides a method for preparing a pigment using the mutant.

Furthermore, the present invention provides a method for preparing a food or feed raw material, including: culturing the mutant.

Advantageous Effects

Through the present invention, it could be confirmed that three mutants were constructed by using the CRISPR gene scissors technology (RGEN RNPs) without any introduction of an exogenous DNA in a microalga *Chlamydomonas reinhardtii* to knock out a ZEP gene, and the amount of zeaxanthin which is an industrially useful pigment was significantly increased when cellular characteristics of the existing wild type and the three mutants of the present invention were compared with each other. In particular, since a DNA fragment is not likely to be inserted into a target base sequence or a base sequence other than the target, it is expected that the procedure of constructing the mutant is not regulated as a GMO, so that it is expected that the procedure of constructing the mutant can create a big economic effect in terms of an industry which produces lutein and zeaxanthin by using microalgae.

DESCRIPTION OF DRAWINGS

The patent or application file contains at least one drawing executed in color. Copies of this patent or patent application publication with color drawings will be provided by the Office upon request and payment of the necessary fee.

The above and other objects, features and advantages of the present invention will become more apparent to those of ordinary skill in the art by describing in detail exemplary embodiments thereof with reference to the accompanying drawings, in which:

FIG. 1 illustrates a general summary on the techniques and methods applied in the present invention;

FIG. 2 illustrates information on a zeaxanthin epoxidase (ZEP) gene of *Chlamydomonas reinhardtii* cw15 wild type (SEQ ID NO: 1);

FIG. 3 is a summary of five target sequences designed for targeting the *Chlamydomonas reinhardtii* ZEP gene (CACCAGCTGCGCGACCGAGCTGG, SEQ ID NO: 12; GCCGTTGCACTTCTGAAGCAGGG, SEQ ID NO: 13; TCCGGCGAACGCACCTGGATGGG, SEQ ID NO: 14; TGGTGGGCGCCGACGGCATCTGG, SEQ ID NO: 15; CCATGGCTTCGCAGGCATCTCGG, SEQ ID NO: 16) [5 sgRNAs were carefully designed within the half of a coding sequence region of a ZEP gene which is different from any other target sites by 3 nucleotides (nt) in the entire genome and has an out-of-frame score higher than 66 by using Cas-Designer (www.rgenome.net/cas-designer/). The 'coding sequence (CDS) position' refers to a relative position of an excision point in a RNA transcript. a + direction refers to a direction which is the same as a target sequence, that is, means that the same sequence is a sequence of RGEN, and – refers to a direction reverse to the target sequence, that is, a sequence having a reverse complement relationship with each other, which is a sequence bound to the target sequence. The out-of-frame score' indicates the probability of a frame shift-inducing deletion occurring when a cleaved double-stranded DNA is repaired by a microhomology-mediated end joining (MMEJ) pathway. The '# of a target-off site' refers to the number of sequences mismatched throughout the entire genome. The linking of the remaining sgRNA sequence (gttttagagctagaaatagcaagttaaaataaggctagtccgttat-caacttgaaaaagtggcaccgagtcggtgc) (SEQ ID NO: 10) to the target sequence results in the entire sgRNA];

FIG. 4 illustrates mutations of a ZEP gene induced by DNA-free RGEN RNPs [a: RGEN-transfected cell and wild-type mutation (insertion and deletion; indel) frequencies for each sgRNA were measured by targeted deep sequencing. The Indel frequency was measured up to about 0.46%. b: a representative mutant DNA sequence (RGEN3) obtained from the third sgRNA having the highest efficiency observed from the targeted deep sequencing analysis result of a, that is, TCCGGCGAACGCACCTGGATGGG (SEQ ID NO: 11). Various indel patterns identified from the target sequence by the targeted deep sequencing analysis result appearing at the 3nt upstream of the PAM sequence. The 20-bp target sequence was underlined and the PAM sequence was indicated in bold.]. The depicted nucleotide sequences, listed from top to bottom, are SEQ ID NOs: 17-22;

FIG. 5 illustrates the Cas9 protein sequence used in Example 1 (SEQ ID NO: 9);

FIG. 6 is a set of photographs illustrating morphological characteristics of a *Chlamydomonas reinhardtii* cw15 wild-type alga and *Chlamydomonas reinhardtii* mutants ΔZ1, ΔZ2, and ΔZ3 [a: measurement of chlorophyll (Chl) fluorescence for several hundreds of colonies to study ZEP gene knock-out, b: a photograph of cultivation in a colony state in a solid TAP medium containing agar, c: a photograph illustrating a state when the concentration was adjusted to the same concentration (OD 750=1) after a *Chlamydomonas reinhardtii* cw15 wild-type alga and *Chlamydomonas reinhardtii* mutants ΔZ1, ΔZ2, and ΔZ3 were liquid-cultured in an HS medium];

FIG. 7 identifies variations in target DNA sequences of actual ZEP gene positions in the three ZEP mutants generated by DNA-free RGEN RNPs [a: wildtype (SEQ ID NO: 23), b: ZEP mutant 1 (ΔZ1) (SEQ ID NO: 24), c: ZEP mutant 2 (ΔZ2) (SEQ ID NO: 25), d. ZEP mutant 3 (ΔZ3) (SEQ ID NO: 26)];

FIG. 8A illustrates information on the ZEP gene of the *Chlamydomonas reinhardtii* mutant ΔZ1 (SEQ ID NO: 3);

FIG. 8B illustrates information on the ZEP gene of the *Chlamydomonas reinhardtii* mutant ΔZ2 (SEQ ID NO: 5);

FIG. 8C illustrates information on the ZEP gene of the *Chlamydomonas reinhardtii* mutant ΔZ3 (SEQ ID NO: 6);

FIG. 9 illustrates autotrophic culture vessels;

FIG. 10 illustrates mixotrophic culture vessels;

FIG. 11 is a set of HPLC analysis graphs illustrating pigment profiles of the *Chlamydomonas reinhardtii* cw15 wild-type and the *Chlamydomonas reinhardtii* mutants ΔZ1, ΔZ2, and ΔZ3 [neo+lor: neoxanthin+loroxanthin, vio: violaxanthin, an: antheraxanthin, lut: lutein, zea: zeaxanthin, chl a: chlorophyll a, chl b: chlorophyll b, α-car: α-carotene), and β-car: β-carotene];

FIG. 12 is a graph illustrating the growth curves (the number of cells per volume, cells/ml) of the *Chlamydomonas reinhardtii* cw15 wild-type and the *Chlamydomonas reinhardtii* mutants ΔZ1, ΔZ2, and ΔZ3 over time;

FIG. 13 is a set of graphs comparing the amounts of lutein and zeaxanthin pigments produced by the *Chlamydomonas reinhardtii* cw15 wild-type (WT) and the ZEP knock-out mutants ΔZ1, ΔZ2, and ΔZ3 over time [a: the amount (mg/L) of lutein produced over time, b: the amount (mg/L) of zeaxanthin produced over time, c: the sum (mg/L) of the amounts of lutein and zeaxanthin produced over time]; and FIG. 14 compares the contents of zeaxanthin and lutein among higher plants known to have high contents of zeaxanthin and lutein, the *Chlamydomonas reinhardtii* cw15 wild-type (WT), and the *Chlamydomonas reinhardtii* ZEP knock-out mutants ΔZ1, ΔZ2, and ΔZ3.

BEST MODE

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

However, the present invention may be modified in various forms and may have various forms, so that specific examples and descriptions set forth below are included merely for aiding the understanding of the present invention, and are not intended to limit the present invention to a specific disclosure form. It should be understood that the scope of the present invention includes all the modifications, equivalents, and replacements falling within the spirit and technical scope of the present invention.

Hereinafter, the present disclosure will be described in more detail.

The present relates to a *Chlamydomonas reinhardtii* mutant.

The *Chlamydomonas reinhardtii* is a eukaryote distributed in various environments such as fresh water and oceans as a unicellular green alga (Chlorophyta), and has a doubling time of 6 to 8 hours. Further, the *Chlamydomonas reinhardtii* is one of the microalgae model systems most widely distributed and can be produced in a bioreactor.

The mutant was constructed by using RGEN RNPs which is not a general mutation treatment, that is, the CRISPR gene scissors technology in which exogenous DNAs are not introduced to knock out zeaxanthin epoxidase (ZEP) genes.

The mutant is a mutant (hereinafter, referred to as ΔZ1) having a ZEP gene mutation in which a base sequence (gaaattaata agactcatta tattccggcg aacgcacctg ga) represented by SEQ ID NO: 2 is inserted between a 816th base and a 817th base in a ZEP gene sequence of a *Chlamydomonas reinhardtii* cw15 WT represented by SEQ ID NO: 1. That is, the mutant is a mutant having a ZEP gene mutation represented by SEQ ID NO: 3.

Further, the mutant is a mutant (hereinafter, referred to as ΔZ2 having a ZEP gene mutation in which a base sequence (tagctctaaa acatccaggt gcgttcgccg gactatagtg agta) represented by SEQ ID NO: 4 is inserted between a 816th base and a 817th base in a ZEP gene sequence of a *Chlamydomonas reinhardtii* cw15 WT represented by SEQ ID NO: 1. That is, the mutant is a mutant having a ZEP gene mutation represented by SEQ ID NO: 5.

In addition, the mutant is a mutant (hereinafter, referred to as ΔZ3) having a ZEP gene mutation in which a base A is inserted between a 816th base and a 817th base in a ZEP gene sequence of a *Chlamydomonas reinhardtii* cw15 WT represented by SEQ ID NO: 1. That is, the mutant is a mutant having a ZEP gene mutation represented by SEQ ID NO: 6.

The three *Chlamydomonas reinhardtii* mutants of the present invention each have an ability to produce a pigment, specifically, an ability to produce xanthophylls. Specifically, the three *Chlamydomonas reinhardtii* mutants of the present invention may have an ability to produce lutein and zeaxanthin. More specifically, the three *Chlamydomonas reinhardtii* mutants of the present invention may have an ability to produce one or more pigments selected from the group consisting of lutein and zeaxanthin; and chlorophyll b, chlorophyll a, and β-carotene.

Since the mutant has a significantly high ability to produce zeaxanthin per cell as compared to the conventional *Chlamydomonas reinhardtii* cw15 wild-type and a content of lutein and zeaxanthin which is more than 12 times higher than those of higher plants known to have a high content of lutein and zeaxanthin [see FIG. 14], there is an advantage in that the mutant can be effectively used as an alga for producing xanthophyll.

In a specific exemplary embodiment, it was confirmed that the mutant of the present invention had a significantly increased amount of zeaxanthin produced over time as compared to the *Chlamydomonas reinhardtii* cw15 wild-type (FIG. 13B), so that it could be seen that the mutant of the present invention had mycological properties having an excellent ability to produce xanthophylls, particularly, zeaxanthin, and it was confirmed that the mutant of the present invention could be effectively utilized as a source of producing a xanthophyll pigment by utilizing the mycological properties.

The mutant of the present invention can survive in dim light, and may be cultured under light intensity conditions specifically within a range of 10 to 2,000 µmol photons/$m^2$s. The mutant cannot photosynthesize in complete darkness which is equal to or less than the dim light conditions, and cell can be damaged by lighting stress under excessive lighting conditions. When the mutant of the present invention is cultured under the conditions, there is an advantage in that the mutant of the present invention has an excellent growth rate while increasing the content of a xanthophyll in the mutant.

The mutant can be appropriately grown within typical growth environments (light intensity conditions, temperature conditions, medium, and the like) of a *Chlamydomonas reinhardtii* alga. Furthermore, since the mutant has an excellent ability to accumulate zeaxanthin even under low light intensity (FIG. 13), the mutant can be industrially and effectively as a xanthophyll pigment-producing microorganism due to the excellent ability to produce a xanthophyll, and the density thereof in a cluster is relatively lower than other algae even under high light intensity, so that the mutant has an effect of having an excellent efficiency of producing a pigment by photosynthesis in a single cell. Specifically, the *Chlamydomonas reinhardtii* wild-type produces almost no zeaxanthin, but the mutant of the present invention has a content of zeaxanthin, which is higher by about 50 times or more than that of the wild-type.

The mutant can be cultured in an environment capable of culturing a general *Chlamydomonas reinhardtii* alga, and specifically, it is possible to use a culture medium capable of culturing an alga under weak light intensity conditions. In order to culture a specific microorganism, the culture medium contains nutritional materials required by a subject to be cultured, that is, a microorganism to be cultured, and may be a culture medium in which a material for a special purpose is additionally added and mixed. The medium also refers to a culture medium or a culture solution, and is a concept encompassing all of the natural medium, the synthetic medium or the selective medium. The *Chlamydomonas reinhardtii* mutant may be cultured according to a typical culture method. For example, the *Chlamydomonas reinhardtii* mutant may be cultured in an HS medium or a TAP medium, which is a photosynthesis medium, and a carbon source may be added. In an exemplary embodiment, it was confirmed that in the culture solution composition environments in Table 1 in the Examples of the present invention, the mutant of the present invention had an excellent ability to produce zeaxanthin.

A pH of the culture medium is not particularly limited as long as the pH is within a range enabling *Chlamydomonas reinhardtii* to survive and be grown, and as an example, a pH of 6 or more, specifically, *Chlamydomonas reinhardtii* can survive within a PH of 6 to a pH of 9, and may have an optimal growth rate at a pH of 7.0 or more and a pH of less than 8.0.

The mutant may be constructed by treating an existing mutagen or using the CRISPR gene scissors technology without introducing an exogenous DNA into a wild-type strain which is not a gene recombinant mutant through introduction of an exogenous gene to directly introduce RGEN RNPs into a target sequence in a ZEP gene.

The *Chlamydomonas reinhardtii* mutant of the present invention can accumulate a pigment, particularly, a xanthophyll-based pigment in the cells, and can include zeaxanthin in an even higher content among the pigments, so that the alga is cultured, and thus can be effectively used as a raw material for a food, feed, a medicine, and the like.

In this regard, the present invention relates to a culture of the *Chlamydomonas reinhardtii* mutant.

In the present invention, "a culture" refers to a medium in which a specific microorganism is cultured, that is, a post-culture medium, and the culture refers to a culture including the *Chlamydomonas reinhardtii* mutant. Further, the culture refers to a culture including all of the concentrate of the culture where a post-culture medium is subjected to processing such as concentration and drying, or the dry material of the culture. The culture can include a byproduct thereof, the preparation thereof is not limited, and as an example, the culture may be a liquid or a solid.

In order to culture a specific microorganism, the medium contains nutritional materials required by a subject to be cultured, that is, a microorganism to be cultured, and may be a medium in which a material for a special purpose is additionally added and mixed. The medium also refers to a culture medium or a culture solution, and is a concept encompassing all of the natural medium, the synthetic medium or the selective medium. A pH of the medium may be more than a range in which a *Chlamydomonas reinhardtii* mutant can be grown, and may be a pH of 6 or more as an example, and preferably a pH of 6 to 9.

Further, the present invention relates to a composition including one or more selected from the group consisting of the *Chlamydomonas reinhardtii* mutant of the present invention, a culture of the alga, a dry material thereof, and an extract thereof.

The composition may be used for improving the health of a human and an animal.

Since the mutant of the present invention has characteristics of producing a xanthophyll-based pigment including zeaxanthin and lutein and accumulating the pigment in vivo, the composition may be a pigment composition or a xanthophyll pigment composition in this regard.

The pigment composition may be a composition in which zeaxanthin is included in an amount of 5 to 15 parts by weight based on 100 parts by weight of the total pigments included in the composition. According to an exemplary embodiment of the present invention, as a result of measuring the content of zeaxanthin in the total pigments per each cell of the *Chlamydomonas reinhardtii* wild-type alga and the *Chlamydomonas reinhardtii* mutant, it could be confirmed that the *Chlamydomonas reinhardtii* mutant had a significantly high content of zeaxanthin in the pigment even when compared to the wild-type (FIG. 13C).

The pigment composition may be used as a raw material for a food or feed, and may be used as a preparation for oral administration.

Accordingly, a pigment composition or xanthophyll pigment composition including the composition or extract may be a composition for oral administration, in that the pigment composition or xanthophyll composition included in a food, a medicine, feed, or the like may be supplied via an oral route.

The composition for oral administration may be included in a formulated oral preparation by using a method publicly known in the art, such as a powder, a granule, a tablet, a pill, a sugar-coated tablet, a liquid, a gel, a syrup, a slurry, and a suspension. For example, for the oral preparation, a tablet or a purified material of sugar may be obtained by blending an active ingredient with a solid excipient, pulverizing the same, adding a suitable auxiliary agent thereto, and then processing the same into a granular mixture. Examples of a suitable excipient include sugars including lactose, dextrose, sucrose, sorbitol, mannitol, xylitol, erythritol, maltitol, and the like, starches including corn starch, wheat starch, rice starch, potato starch, and the like, celluloses including cellulose, methyl cellulose, sodium carboxymethyl cellulose, hydroxypropylmethyl cellulose, and the like, and fillers such as gelatin and polyvinylpyrrolidone. In addition, a crosslinked polyvinylpyrrolidone, agar, alginic acid, sodium alginate, or the like may be added as a disintegrating agent in some cases.

Furthermore, the composition can be added in order to achieve a purpose use which is special for a food or feed, and thus may be a food composition, a composition for a food additive, a feed composition or a composition for a feed additive. When the composition is used for feed or a food, health in the body can be maintained or strengthened by a xanthophyll pigment, particularly, zeaxanthin and lutein produced by the *Chlamydomonas reinhardtii* mutant and accumulated in the cells. Specifically, the zeaxanthin and lutein can prevent or alleviate degeneration of the macula, and the like as a macular pigment, and thus are effective for preventing or alleviating eye disorders related to the macular degeneration. More specifically, since the zeaxanthin and lutein have effects of strengthening or maintaining eye health; preventing or alleviating the macular degeneration; preventing or alleviating deterioration in eye function; alleviating or preventing damage to the retina; suppressing aging; maintaining retinal health; reducing the risk of developing the macular degeneration; or preventing or alleviating failing eyesight, the feed or food composition may be used for the use of preventing or alleviating the symptoms or the effects.

In the present invention, "for an additive" includes all food compositions as long as the food composition is a constitution in which ingredients other than the main ingredient are added to a food or feed, and a specific example thereof may be an effectively active material having functionality in a food or feed or a food additive defined by the Ministry of Food and Drug Safety of Republic of Korea to be added for coloring, preservation, and the like in a processed food.

The food may be a health functional food. More specifically, the food may be a food functional food for eye health.

The food, the food additive, the feed or the composition for a feed additive may further include other effective ingredients within a range not impairing the activity of the *Chlamydomonas reinhardtii* mutant of the present invention, a culture of the mutant, a dry material thereof, and an extract thereof. Further, it is possible to further include an additional ingredient such as a carrier.

In the present invention, a composition for feed may be prepared in the form of fermented feed, blended feed, a pellet, silage, and the like. The fermented feed may be prepared by including the *Chlamydomonas reinhardtii* mutant of the present invention, a dry fungus body of the mutant, a culture of the mutant, and an extract thereof, and additionally include various microbial bacteria or enzymes. The blended feed may be prepared by including various types of general feed, the mutant of the present invention, a dry fungus body of the mutant, a culture of the alga, and an extract thereof and mixing the mixture. A feed in the form of a pellet may be prepared by formulating the fermented feed or blended feed with a pellet machine. The silage may be prepared by mixing silage with a *Chlamydomonas reinhardtii* mutant, a dry fungus body of the mutant, a culture of the mutant and/or an extract thereof, but the use of the composition of the present invention is not limited thereto.

The composition may be mixed with a carrier and a flavoring typically used in the food or pharmaceutical field and may be prepared and administered in the form of a tablet, a troche, a capsule, an elixir, a syrup, a powder, a suspension, a granule, or the like. As the carrier, it is possible to use a binder, a lubricant, a disintegrating agent, an excipient, a solubilizing agent, a dispersing agent, a stabilizing agent, a suspending agent, and the like. As an administration method, an oral, parenteral, or application method may be used, but preferably, it is preferred that the composition is orally administered. In addition, an administration dose may be appropriately selected depending on the absorption degree, the inactivation rate and the excretion rate of an active ingredient in the body, and age, gender, status, and the like of a person to be treated. A pH of the composition can be easily changed depending on the production conditions and the like of medicine, food, and the like in which the composition is used.

The composition may include any one selected from the group consisting of a *Chlamydomonas reinhardtii* mutant, a culture of the mutant, a dry material thereof, and an extract thereof in an amount of 0.001 to 99.99 wt %, preferably 0.1 to 99 wt %, based on the total weight of the composition, and the content of an active ingredient may be appropriately adjusted depending on the method for using the composition and the purpose of using the composition.

The *Chlamydomonas reinhardtii* mutant may be included as it is or in a dried form in the composition, and the culture of the alga may be included in a concentrated or dried form in the composition. Furthermore, the dry material refers to a dried form of the alga or the culture thereof, and may be in the form of a powder prepared by lyophilization, and the like.

Further, the extract refers to an extract obtained by extracting a product from the *Chlamydomonas reinhardtii* mutant of the present invention, a culture solution thereof, or a dry material thereof, and includes an extract using a solvent, and the like, and an extract obtained by crushing the *Chlamydomonas reinhardtii* mutant of the present invention. Specifically, the extract may be an extract obtained by extracting and separating a pigment accumulated in the cells of the *Chlamydomonas reinhardtii* mutant of the present invention by a physical or chemical method.

The extraction procedure may be carried out by a typical method, and as an example, a target pigment may be extracted by adding an extraction solvent to the *Chlamydomonas reinhardtii* mutant of the present invention, homogenizing the resulting mixture, and then crushing the fungus body. After the extraction, a crushed material of the alga may be removed through centrifugation, and the extraction solvent may be removed by a method such as distillation under reduced pressure. In addition, the extraction procedure may further include a typical purification process. The aforementioned pigment has a property of being insoluble in water, and thus can be more easily extracted from the alga of the present invention.

Since the *Chlamydomonas reinhardtii* mutant of the present invention has an excellent ability to produce a xanthophyll, particularly zeaxanthin at low light intensity, a compound including the mutant and a byproduct thereof has effects of improving body activity, maintaining body functionality, and preventing deterioration in body functionality. Specifically, since the xanthophyll pigment is known to have an effect of suppressing macular degeneration, antioxidant and anticancer effects, and the like, the composition of the present invention may be used as a raw material included in a food, a health functional food, a medicine, feed, and the like for the use of maintaining body health, specifically, maintaining the body function with which the xanthophyll pigment is associated, preventing deterioration in body function, or improving the body function.

Furthermore, another object of the present invention is to provide a method for preparing a pigment using the *Chlamydomonas reinhardtii* mutant of the present invention.

Further, still another object of the present invention is to provide a method for preparing a food or feed raw material, including: culturing the *Chlamydomonas reinhardtii* mutant of the present invention.

When the *Chlamydomonas reinhardtii* mutant of the present invention is used, an amount of xanthophylls accumulated in the algae to be cultured may be increased, so that the supply of a raw material industrially used, and the like may be efficiently carried out.

The preparation method may include culturing the *Chlamydomonas reinhardtii* mutant of the present invention.

In addition, the preparation method may further include: separating the *Chlamydomonas reinhardtii* mutant of the present invention from the culture, after the culturing of the *Chlamydomonas reinhardtii* mutant of the present invention. The separated algae may be further subjected to a processing step including drying.

Furthermore, the preparation method may further include: extracting a pigment from the *Chlamydomonas reinhardtii* mutant of the present invention, a concentrate of the culture, or a dry material of the culture.

The culturing may be carried out in a medium under a pH condition of 6.0 to 8.0. Further, the culturing may be carried out under weak lighting conditions, specifically, under light intensity conditions within a range of 10 to 2,000 μmol photons/m$^2$s. The *Chlamydomonas reinhardtii* mutant of the present invention has an excellent ability to produce a pigment even at low light intensity, and thus may increase the content of xanthophylls in the body, so that an excellent accumulation of xanthophylls may be achieved without inputting energy at high light intensity, and as a result, the *Chlamydomonas reinhardtii* mutant of the present invention may be industrially and effectively used.

The extraction may be carried out by a typical method such as a method for extracting a pigment from microorganisms, and examples thereof include an enzyme method, an ultrasonic extraction method, a mechanical extraction method, and the like, and are not limited thereto.

The preparation method may further include, in addition to the culturing step, a concentrating step of increasing the content of the alga after the culturing and a drying step of drying the alga subjected to the concentrating step by further reducing moisture in the alga. However, the concentrating step or the drying step is not necessarily needed, and may be generally carried out by using a concentrating and drying method, and a machine typically used in the field to which the present invention belongs.

The preparation method may be carried out by further including a purification step after the extracting step, and the purification step may be carried out by a typical purification method in the field to which the present invention belongs.

Xanthophylls prepared through the concentrating or drying step may be used as a raw material for a food, a health functional food, a cosmetic, a medicine, or the like.

The method for preparing xanthophylls may be carried out by adopting other methods within a range not impairing the effects of the present invention.

The contents on the mutant and the composition may also be applied mutatis mutandis to the preparation method of the present invention.

Hereinafter, the present invention will be described in detail through the Examples. However, the following Examples are only for exemplifying the present invention, and the scope of the present invention is not limited to the following Examples. The present Examples are provided to make the disclosure of the present invention perfect and to make a person skilled in the art to which the present invention belongs perfectly comprehend the scope of the present invention, and the present invention is defined only by the scope of the claims.

EXAMPLES

Example 1: Construction of ZEP Gene Knock-Out Mutant

In order to target a ZEP gene of *Chlamydomonas reinhardtii* (phytozome: Cre02.g082550 or NCBI: AY211267.1) [phytozome.jgi.doe.gov/pz/portal.html#!gene?search=1&detail=1&method=4614&searchText=transcriptid: 30785220, present at a position of 1244277-1250969 in chromosome #2], for an sgRNA, five sgRNAs which allow the induction of a microhomology-driven frameshift mutation by using Cas-Designer (www.rgenome.net) were designed, and were synthesized through an in vitro transcription method. FIG. 3 is a description on the target sequences of the five sgRNAs constructed for targeting the ZEP gene. A Cas9 protein was prepared by expressing a recombinant Cas9 protein using *E. coli*, and performing purification. A *Chlamydomonas reinhardtii* cw15 mt-wild-type (CC-4349) used in the experiment was secured through the *Chlamydomonas* Resource Center (chlamycollection. org) [www.chlamycollection.org/product/cc-4349-cw15-mt-goodenough-330a/]. The *Chlamydomonas* cells were put into a 25° C. 50-ml flask containing a TAP medium [see Table 2], and were cultured while being irradiated with light using a fluorescence lamp at a light intensity of 70 uE and being shaken at 90 rpm. The concentration of the cells was measured by using a spectrophotometer, and cells during a period of actively culturing to an $OD_{750}$ of approximately 0.3 to 0.5 were used. In order to make a complex of RNPs, 200 ug of the Cas9 protein (FIG. 5, SEQ ID NO: 9) was mixed with 140 ug of the sgRNA (SEQ ID NO: 8) in nuclease-free water, and incubated at room temperature for 10 minutes. After the complex of the bound RNPs was transformed along with 50×10$^4$ *Chlamydomonas reinhardtii* cw15 mt-wild-type (CC-4349) cells through (voltage 600 V, Capacity 50 μF) electric shock in a 4 mm electroporation cuvette by using a Biorad Gene Pulser Xcell™ electroporation system, the complex was subjected to gDNA extraction after dark incubation for 12 hours, and analyzed by performing targeted deep sequencing, and a single colony was obtained by diluting a part of the complex with 2,000 cells and streaking and spreading the diluted solution on a TAP agar plate. FIG. 4 is a result identifying the mutation of the ZEP gene, which was induced by RGEN-RNPs due to the targeted deep sequencing. The mutation of a target gene was identified by separating the single colony induced by the third sgRNA (0.456%) where the transformation efficiency was at the highest level. (Panel b of FIG. 4 illustrates the data of the targeted deep sequencing and of an experiment in which when the entire cells are collected and gDNAs are extracted and analyzed after the transformation experiment using the RNPs, all the mutations occurring in the DNA strands of a target site for the entire cells are analyzed, and the pattern and frequency thereof can be seen. That is, panel b of FIG. 4 illustrates patterns of the mutation actually identified at the target site through the targeted deep sequencing, but it is difficult to find out a big size change such as insertion of 42 bp or more by a principle of the targeted deep sequencing, and there may be a difference from a single colony actually obtained)

After the ZEP specific knock-out mutant was produced in this manner by using DNA-free RGEN RNPs, the Chl fluorescence with respect to all the cells was measured in the petri dish, and several estimated ZEP knock-out cell lines were selected. A circular shape indicates an estimated ZEP knock-out mutant grown on a TAP agar medium under dim light (50 μmol photons/m$^2$s) conditions [Panel a of FIG. 4]. NPQ/4 images were measured by Imaging PAM (Walz). Unicellular colonies of the wild-type (WT) and AZEP mutant cell lines were grown on a minimum agar medium under dim light (50 μmol photons/m$^2$s) conditions [Panes a and b of FIG. 6]. Among the thus-identified colonies, three mutants (ΔZ1, ΔZ2, and ΔZ3) where the content of the macular pigment was increased were selected, and a change in target DNA sequence at the actual position of the ZEP position was identified from the three ZEP mutants generated by RGEN RNPs through Sanger sequencing [FIG. 7].

As illustrated in FIG. 6b, it could be confirmed that the colonies of the *Chlamydomonas reinhardtii* cw15 wild-type and the mutants ΔZ1, ΔZ2, and ΔZ3 were grown in forms and sizes similar to one another on the TAP agar plate under the same light intensity conditions. Further, in the case of the cells liquid-cultured through photosynthesis in an HS medium, it can be confirmed that at the same concentration of the cells, the *Chlamydomonas reinhardtii* wild-type exhibits a striking green color, whereas the mutants ΔZ1, ΔZ2, and ΔZ3 exhibit a green color similar to a grass color tone [panel c of FIG. 6].

Among the selected mutants, the mutant Z1 was named as *Chlamydomonas reinhardtii* ZEP mutant 1 (ΔZ1), and the mutant was deposited at the Korean Collection for Type Cultures (KCTC), Korea Research Institute of Bioscience & Biotechnology on Mar. 22, 2017 and given Accession No. KCTC 13230BP.

Example 2: Culturing of Mutant

1) Autotrophic Culture

In the case of an autotrophic culture in which the mutant was cultured in a state where an external carbon source was not supplied and by using only photosynthesis, the mutant was cultured in an HS medium which is a minimum medium by supplying 5% $CO_2$. After a medium having the composition as in the following Table 1 was produced, the medium was autoclaved and prepared, and the growth was initiated by making the concentration become 10$^6$ cells/mL in the culture solution using cells in an active growth stage. A culture vessel was supplied with bubbles from beneath using a column made of glass as in FIG. 9, and was irradiated with light using a fluorescence lamp at a light intensity of 200 uE from both sides.

TABLE 1

| HS Media Ingredients | Con. in culture solution (nM or μM) |
|---|---|
| Buffer and Major Ingredients (nM) | |
| $NH_4Cl$ | 9.345 |
| $MgSO_4·7H_2O$ | 0.08 |
| $CaCl_2·2H_2O$ | 0.07 |
| $K_2HPO_4$ | 8.265 |
| $KH_2PO_4$ | 5.29 |
| Trace Ingredients (μM) | |
| $ZnSO_4·7H_2O$ | 765 |
| $H_2BO_2$ | 922 |
| $MnCl_2·4H_2O$ | 511 |
| $CoCl_2·6H_2O$ | 7 |
| $CuSO_4·5H_2O$ | 126 |
| $(NH_4)_2Mo_7O_{24}·4H_2O$ | 18 |
| $PeSO_4·7H_2O$ | 18 |
| EDTA disodium salt | 184 |
| Others | |
| Carbon Source | 5% $CO_2$ bubble, 80 cc/min |
| pH in Culture Solution | 7.0 |
| Light Intensity | 200 uE |

2) Mixotrophic Culture

In the case of performing a mixotrophic culture where the mutant was cultured by supplying both photosynthesis and a carbon source, the mutant was cultured by adding acetic acid to a TAP medium. After a medium having the composition as in the following Table 2 was produced, the medium was autoclaved and prepared, and the growth was initiated by making the concentration become 10$^6$ cells/mL in the culture solution using cells in an active growth stage. For the culture vessels, the mutant was cultured at large volumes by using a flask or bottle made of glass as in FIG. 10, and was stirred by using a magnetic bar. The mutant was together irradiated with light using a fluorescence lamp at a light intensity of 70 uE.

TABLE 2

| TAP Media Ingredients | Con. in culture solution (nM or μM) |
|---|---|
| Buffer and Major Ingredients (nM) | |
| $NH_4Cl$ | 7.5 |
| $CaCl_2·2H_2O$ | 0.675 |
| $MgSO_4·7H_2O$ | 0.8 |
| $K_2HPO_4$ | 0.62 |
| $KH_2PO_4$ | 0.41 |
| Trace Ingredients (μM) | |
| $EDTA·2H_2O$ | 185 |
| $FeSO_4·7H_2O$ | 18 |
| $ZnSO_4·7H_2O$ | 75 |
| $H_2BO_2$ | 185 |
| $MnCl_2·4H_2O$ | 26 |
| $CuCl_2·2H_2O$ | 6.5 |
| $Na_2MoO_4·2H_2O$ | 5.5 |
| $CoCl_2·6H_2O$ | 6.5 |
| Others | |
| Carbon Source | Glacial acetic acid, 1 ml/L |
| Tris | 2.42 g/L |
| pH in Culture Solution | 7.2 |
| Light Intensity | 70 uE |

Example 4: Pigment Analysis of Mutant and Identification of Growth Characteristics 1) Pigment Analysis of Mutant After a separation into a single colony as in Example 1, the mutant was continuously cultured, and a pigment analysis of each colony was carried out by using HPLC.

Specifically, the separated single colonies were cultured in a TAP medium under 70 µmol photons/m$^2$s conditions for 3 days, and the specific culture conditions were carried out as under the culture conditions in 2) of Example 2. From the harvested alga, a pigment was extracted by using 80% acetone, and a centrifuged supernatant was filtered again by using a nylon filter, and then injected into an HPLC and analyzed.

Specifically, in order to separate the pigment, the total flow rate of the solvent was set at 1.2 mL per minute, and Tris with a pH of 8.0 and acetonitrile were each uniformly decreased from 14% and 84% to 0% from the 0th minute to the 15th minute, and methanol and ethyl acetate were increased starting from 2% to 68% and 32%, respectively, up to the 15th minute. Thereafter, this solvent ratio was maintained as it was for 3 minutes (from the 15th minute to the 18th minute), and then the ratio of each solvent was returned to the ratio at the start for 1 minute (from the 18th minute to the 19th minute), and then a post-run was performed while maintaining the solvent ratio as it was for the remaining 6 minutes. Shimadzu LC-20A Prominence manufactured by Shimadzu Company was used as a pump, Watera Spherisorb TMS5 (DS1 4.6×250 mm, 5 µm Cartridge Column, USA) was used as a column, and the temperature of the column was maintained at 40° C. Data was analyzed by using a photodiode array detector (SPD-M20A, Shimadzu) as a detector, and the concentrations were obtained by using a standard curve which quantified a carotenoid and chlorophylls a and b purchased from Agem Alle, Horsholm, Denmark (DHL) as a standard from the result in which carotenoid pigments including zeaxanthin and chlorophyll a were detected at 445 nm and 670 nm, respectively.

FIG. 11 illustrates HPLC analysis graphs illustrating a pigment profile of each alga, and FIG. 13 illustrates a set of graphs which quantitatively analyze the contents of zeaxanthin and lutein of each alga grown under 200 µmol photons/m$^2$s using HPLC.

2) Identification of Growth Rate

In order to compare the cell proliferation rates and final growth amounts of the wild-type *Chlamydomonas reinhardtii* alga and the mutants ΔZ1, ΔZ2, and ΔZ3, the alga and the mutants were cultured under light intensity conditions of 200 µmol photons/m$^2$s in a state where 5% CO2 bubbles were supplied in an HS medium which is a minimum photosynthesis medium [see Table 1]. The number of initially inoculated cells was 1×10$^6$ cells/ml, and a growth curve was drawn by measuring the number of cells at intervals of 12 hours for 60 hours. FIG. 12 is an experimental result of comparing the cell growth rates through photosynthesis using carbon dioxide in the wild-type (WT) and the ZEP knock-out mutants. As illustrated in FIG. 12, it was confirmed that the mutants ΔZ1, ΔZ2, and ΔZ3 had a growth rate at a level similar to the wild-type as the culture period elapsed.

Example 5: Identification of Pigment Production

The contents of lutein and zeaxanthin pigments of the cells were quantitatively analyzed at intervals of 12 hours by using HPLC simultaneously while carrying out the experiment in FIG. 12. Through FIG. 13, the amounts of lutein and zeaxanthin produced from the *Chlamydomonas reinhardtii* cw15 wild-type (WT) and the ZEP knock-out mutants over time were compared with one another. When the results of the ZEP knock-out mutants were compared to those of the wild-type, it could be confirmed that the amounts of lutein produced from the ZEP knock-out mutants were at a level similar to that of the wild-type, but the amounts of zeaxanthin insignificantly present in the wild-type were greatly increased by at least 50 times or more.

The following Table 3 and FIG. 14 compare the contents of zeaxanthin and lutein from higher plants known to have high contents of zeaxanthin and lutein with those from the *Chlamydomonas reinhardtii* cw15 wild-type (WT) and the ZEP knock-out mutants. For the *Chlamydomonas*, the content (µg/100 g) was calculated by dividing the amounts of lutein and zeaxanthin pigments by the dry weight of the cells at 36 hours in FIG. 12. The pigment contents (µg/100 g) of the remaining higher plants known to have high contents of zeaxanthin and lutein were compared by citing the USDA National Nutrient Database for Standard Reference, Release 23 (2010). When the contents of lutein and zeaxanthin were compared with those of the higher plants, the *Chlamydomonas reinhardtii* wild-type exhibited a content which is higher by at least 6 times or more (than that of nasturtium) and the ZEP gene knock-out mutants exhibited a content which is higher by 12 times or more (than that of nasturtium). In particular, when the content of zeaxanthin was compared with those of the higher plants, the ZEP gene knock-out mutants exhibited a content which is higher by at least 120 times or more (than that of orange pepper).

Through FIGS. 13 and 14, high productivities and contents were identified, and through this, it could be confirmed that the mutants had high competitiveness in the raw material market of the lutein and zeaxanthin pigment industry.

TABLE 3

| Product | Lutein + Zeaxanthin (µg/100 g) |
|---|---|
| Chlamydomonas, cw15-, WT | 274,397 |
| Chlamydomonas, ZEP mutant 1 (ΔZ1) | 528,353 |
| Chlamydomonas, ZEP mutant 2 (ΔZ2) | 502,520 |
| Chlamydomonas, ZEP mutant 3 (ΔZ3) | 544,684 |
| Nasturtium (yellow flowers) | 45,000 |
| Kale (raw) | 39,550 |
| Kale (cooked) | 18,246 |
| Dandelion leaves (raw) | 13,610 |
| Nasturtium (leaves) | 13,600 |
| Turnip greens (raw) | 12,825 |
| Spinach (raw) | 12,198 |
| Spinach (cooked) | 11,308 |
| Swiss chard (raw or cooked) | 11,000 |
| Turnip greens (cooked) | 8440 |
| Collard greens (cooked) | 7694 |
| Watercress (raw) | 5767 |
| Garden peas (raw) | 2593 |
| Romaine lettuce | 2312 |
| Zucchini | 2125 |
| Brussels sprouts | 1590 |
| Pistachio nuts | 1205 |
| Broccoli | 1121 |
| Carrot (cooked) | 687 |
| Maize/corn | 642 |
| Egg (hard boiled) | 353 |
| Avocado (raw) | 271 |
| Carrot (raw) | 256 |
| Kiwi fruit | 122 |

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

[Information on Deposit of Microorganism]

Name of Depository Institution: Korea Research Institute of Bioscience & Biotechnology Accession number: KCTC13230BP Deposit date: Mar. 22, 2017

*Chlamydomonas reinhardtii* ZEP mutant 1 (ΔZ1) (accession number: KCTC 13230BP) was deposited with Korea Research Institute of Bioscience and Biotechnology, on Mar. 22, 2017. The subject strain has been deposited under conditions that assure that access to the strain will be available during the pendency of this patent application to one determined by the Commissioner of Patents and Trademarks to be entitled thereto under 37 CFR 1.14 and 35 U.S.C. 122. The deposit will be 10 available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject deposits will be stored and made available to the public in accord with 15 the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit 20 should the depository be unable to furnish a sample when requested, due to the condition of the deposit. All restrictions on the availability to the public of the subject culture deposit will be irrevocably removed upon the granting of a patent disclosing it.

The invention claimed is:

1. A *Chlamydomonas reinhardtii* mutant having a ZEP gene mutation in which a base A is inserted between a 816th base and a 817th base in a ZEP gene sequence of a *Chlamydomonas reinhardtii* represented by SEQ ID NO: 1 and having an ability to produce a xanthophyll.

2. The *Chlamydomonas reinhardtii* mutant of claim 1, wherein the *Chlamydomonas reinhardtii* mutant has a ZEP gene mutation represented by SEQ ID NO: 6.

3. A composition comprising one or more selected from the group consisting of the *Chlamydomonas reinhardtii* mutant of claim 1, a culture thereof, a dried material thereof, and an extract thereof.

* * * * *